United States Patent
Benjamin et al.

(10) Patent No.: US 7,490,382 B2
(45) Date of Patent: *Feb. 17, 2009

(54) CHILD'S SIZED DISPOSABLE ARTICLE

(75) Inventors: Joyce Marie Benjamin, Mason, OH (US); Michael Wayne Mason, Cincinnati, OH (US); Jenna Mason, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 377 days.

This patent is subject to a terminal disclaimer.

(21) Appl. No.: 10/948,491

(22) Filed: Sep. 23, 2004

(65) Prior Publication Data

US 2005/0125924 A1 Jun. 16, 2005

Related U.S. Application Data

(63) Continuation of application No. 10/737,415, filed on Dec. 16, 2003, now abandoned.

(51) Int. Cl.
*A47L 13/19* (2006.01)
(52) U.S. Cl. ..................... 15/104.94; 15/227
(58) Field of Classification Search .............. 15/104.94, 15/209.1, 210.1, 227
See application file for complete search history.

(56) References Cited

U.S. PATENT DOCUMENTS

| | | | |
|---|---|---|---|
| 1,547,179 A | 7/1925 | Martens | |
| 2,798,053 A | 7/1957 | Brown | |
| 2,831,854 A | 4/1958 | Tucker et al. | |
| 3,711,889 A | 1/1973 | Jennings | |
| 3,755,560 A | 8/1973 | Dickert et al. | |
| 3,862,472 A | 1/1975 | Norton et al. | |
| 3,902,509 A | 9/1975 | Tundermann et al. | |
| 3,929,678 A | 12/1975 | Laughlin et al. | |
| 3,963,699 A | 6/1976 | Rizzi et al. | |
| 3,967,756 A | 7/1976 | Barish | |
| 3,982,302 A | 9/1976 | Vaalburg | |
| 3,982,659 A | 9/1976 | Ross | |
| 3,986,479 A | 10/1976 | Bonk | |
| 3,994,417 A | 11/1976 | Boedecker | |
| 4,004,323 A | 1/1977 | Gotchel et al. | |
| 4,005,195 A | 1/1977 | Jandacek | |
| 4,005,196 A | 1/1977 | Jandacek | |
| 4,057,669 A | 11/1977 | McConnell | |
| 4,097,965 A | 7/1978 | Gotchel et al. | |
| 4,130,915 A | 12/1978 | Gotchel et al. | |
| 4,135,024 A | 1/1979 | Callahan et al. | |
| 4,154,542 A | 5/1979 | Rasmason | |
| 4,176,427 A | 12/1979 | Neuenschwander | |
| 4,189,896 A | 2/1980 | Kolbach et al. | |
| 4,207,367 A | 6/1980 | Baker | |

(Continued)

FOREIGN PATENT DOCUMENTS

EP       0068516 A1    1/1983

(Continued)

*Primary Examiner*—Randall Chin
(74) *Attorney, Agent, or Firm*—Matthew P. Fitzpatrick; Sarah Ann Dressel; John G. Powell

(57) ABSTRACT

A disposable child sized article is provided. The disposable child sized article is releasably carrying a benefit composition. An article of commerce comprising disposable child sized article is also provided.

21 Claims, 26 Drawing Sheets

U.S. PATENT DOCUMENTS

| | | | |
|---|---|---|---|
| 4,233,212 A | 11/1980 | Otoi et al. | |
| 4,296,161 A | 10/1981 | Kaiser et al. | |
| 4,309,469 A | 1/1982 | Varona | |
| 4,421,769 A | 12/1983 | Dixon et al. | |
| 4,471,881 A | 9/1984 | Foster | |
| 4,509,949 A | 4/1985 | Huang et al. | |
| 4,510,640 A * | 4/1985 | Omori | 15/104.002 |
| 4,517,360 A | 5/1985 | Volpenhein | |
| 4,518,772 A | 5/1985 | Volpeinhein | |
| 4,523,348 A | 6/1985 | Petrie | |
| 4,599,379 A | 7/1986 | Flesher et al. | |
| 4,628,078 A | 12/1986 | Glover et al. | |
| 4,637,859 A | 1/1987 | Trokhan | |
| 4,682,942 A | 7/1987 | Gotchel et al. | |
| 4,741,855 A | 5/1988 | Grote et al. | |
| 4,797,300 A | 1/1989 | Jandacek et al. | |
| 4,835,206 A | 5/1989 | Farrar et al. | |
| 4,839,165 A | 6/1989 | Hoppe et al. | |
| 4,839,168 A | 6/1989 | Abe et al. | |
| 4,840,270 A | 6/1989 | Caputo | |
| 4,849,484 A | 7/1989 | Heard | |
| 4,893,372 A | 1/1990 | Wenzel | |
| 4,960,764 A | 10/1990 | Figueroa, Jr. et al. | |
| 4,971,220 A | 11/1990 | Kaufman | |
| 4,976,953 A | 12/1990 | Orr et al. | |
| 5,009,813 A | 4/1991 | Watanabe et al. | |
| 5,050,737 A | 9/1991 | Josylin | |
| 5,069,898 A | 12/1991 | Goldberg | |
| 5,087,445 A | 2/1992 | Haffey et al. | |
| 5,100,660 A | 3/1992 | Hawe et al. | |
| 5,107,562 A * | 4/1992 | Dunn | 15/167.1 |
| 5,223,096 A | 6/1993 | Phan et al. | |
| 5,240,562 A | 8/1993 | Phan et al. | |
| 5,306,514 A | 4/1994 | Letton et al. | |
| 5,306,515 A | 4/1994 | Letton et al. | |
| 5,306,516 A | 4/1994 | Letton et al. | |
| 5,322,178 A | 6/1994 | Foos | |
| 5,366,104 A | 11/1994 | Armstrong | |
| 5,369,257 A * | 11/1994 | Gibbon | 219/759 |
| 5,412,634 A | 5/1995 | Buchler et al. | |
| 5,412,830 A | 5/1995 | Girardot et al. | |
| 5,487,884 A | 1/1996 | Bissett et al. | |
| 5,540,976 A | 7/1996 | Shawver et al. | |
| 5,542,566 A | 8/1996 | Glaug et al. | |
| 5,556,509 A | 9/1996 | Trokhan et al. | |
| 5,580,423 A | 12/1996 | Ampulski et al. | |
| 5,605,749 A | 2/1997 | Pike et al. | |
| 5,607,980 A | 3/1997 | McAtee et al. | |
| 5,647,506 A | 7/1997 | Julius | |
| 5,649,336 A | 7/1997 | Finch et al. | |
| 5,686,082 A | 11/1997 | N'Guyen | |
| 5,725,382 A | 3/1998 | Walter et al. | |
| 5,785,179 A | 7/1998 | Buczwinski | |
| 5,791,465 A | 8/1998 | Niki | |
| 5,839,842 A | 11/1998 | Wanat et al. | |
| 5,883,998 A | 11/1998 | Biederman et al. | |
| 5,939,082 A | 8/1999 | Oblong et al. | |
| 5,955,417 A | 9/1999 | Taylor | |
| D414,637 S | 10/1999 | Amundson | |
| D416,794 S | 11/1999 | Cormack | |
| 6,024,970 A | 2/2000 | Woodard | |
| D421,901 S | 3/2000 | Hill | |
| D421,902 S | 3/2000 | Hill | |
| 6,092,690 A | 7/2000 | Bitowft | |
| D437,686 S | 2/2001 | Balzar | |
| 6,200,554 B1 | 3/2001 | Yeoh et al. | |
| 6,206,863 B1 | 3/2001 | Skewes et al. | |
| D443,451 S | 6/2001 | Buck | |
| D443,508 S | 6/2001 | Braaten | |
| 6,248,317 B1 | 6/2001 | Snyder et al. | |
| D445,329 S | 7/2001 | Zethoff | |
| 6,257,785 B1 | 7/2001 | Otten et al. | |
| 6,269,969 B1 | 8/2001 | Huang | |
| 6,269,970 B1 | 8/2001 | Huang | |
| 6,280,751 B1 | 8/2001 | Fletcher et al. | |
| 6,292,949 B1 | 9/2001 | Chang | |
| 6,296,144 B1 | 10/2001 | Tanaka | |
| 6,315,114 B1 | 11/2001 | Keck | |
| D451,279 S | 12/2001 | Chin | |
| 6,335,312 B1 | 1/2002 | Coffindaffer et al. | |
| 6,401,968 B1 | 6/2002 | Huang | |
| 6,412,634 B1 | 7/2002 | Telesca | |
| 6,440,437 B1 | 8/2002 | Krzysik et al. | |
| 6,501,002 B1 | 12/2002 | Roe et al. | |
| 6,506,394 B1 | 1/2003 | Yohiaoui et al. | |
| 6,630,175 B1 | 10/2003 | Shapiro et al. | |
| 6,669,387 B2 * | 12/2003 | Gruenbacher et al. | 401/7 |
| 6,726,386 B1 * | 4/2004 | Gruenbacher et al. | 401/7 |
| 2002/0064323 A1 | 5/2002 | Chin | |
| 2002/0177535 A1 | 11/2002 | Piterski et al. | |
| 2002/0178482 A1 | 12/2002 | Samuelsson et al. | |
| 2003/0130636 A1 | 7/2003 | Brock et al. | |
| 2003/0140439 A1 | 7/2003 | Durden et al. | |
| 2003/0190337 A1 | 10/2003 | Bissett | |
| 2003/0215486 A1 | 11/2003 | Berry et al. | |
| 2003/0217425 A1 | 11/2003 | Datta et al. | |
| 2004/0022833 A1 | 2/2004 | Hartwig et al. | |
| 2004/0118530 A1 * | 6/2004 | Kressner et al. | 162/109 |
| 2005/0042261 A1 | 2/2005 | Hasenoehrl et al. | |
| 2005/0125877 A1 | 6/2005 | Benjamin et al. | |
| 2005/0125923 A1 | 6/2005 | Benjamin et al. | |
| 2005/0129743 A1 | 6/2005 | Benjamin et al. | |
| 2005/0220847 A1 | 10/2005 | Benjamin et al. | |

FOREIGN PATENT DOCUMENTS

| | | |
|---|---|---|
| EP | 0 228 868 A2 | 7/1987 |
| FR | 2 813 777 A | 3/2002 |
| WO | WO 97/38598 A1 | 10/1997 |
| WO | WO 97/39733 A1 | 10/1997 |
| WO | WO 99/55213 A1 | 11/1999 |
| WO | WO 00/27268 A1 | 5/2000 |
| WO | WO 01/08641 A | 2/2001 |
| WO | WO 02/14172 A1 | 2/2002 |
| WO | WO 03/000106 A1 | 1/2003 |
| WO | WO 2004/080256 A1 | 9/2004 |
| WO | WO 2004/080257 A1 | 9/2004 |
| WO | WO 2004/080258 A1 | 9/2004 |

* cited by examiner

CHILD'S SIZED DISPOSABLE ARTICLE

CROSS REFERENCE TO RELATED APPLICATION

This application is a continuation of application Ser. No. 10/737,415, filed Dec. 16, 2003 now abandoned.

COPYRIGHT NOTICE

A portion of the disclosure of this patent document contains material which is subject to copyright and/or trademark protection. The copyright and trademark owner has no objection to the facsimile reproduction by anyone of the patent document or the patent disclosure, as it appears in the Patent and Trademark Office patent file or records, but otherwise reserves all copyright and trademark rights whatsoever.

FIELD OF INVENTION

A disposable child sized article is provided. The disposable child sized article is releasably carrying a benefit composition.

BACKGROUND OF THE INVENTION

Consumer products, such as, cleansing and conditioning products as well as household consumer cleaning products, have traditionally been marketed in a variety of forms such as bar soaps, creams, foams, sprays, liquids, powders, lotions, and gels. Typically, these products must satisfy a number of criteria to be acceptable to consumers. These criteria include effectiveness, skin feel, mildness to skin, suitability for use in the consumer's household, and appearance. Typically these consumer products comprise a benefit composition in some form.

It is highly desirable to deliver benefit compositions from a disposable substrate. Disposable products are convenient because they obviate the need to carry or store cumbersome bottles, bars, jars, tubes, and other forms of clutter associated with consumer products. Disposable products are also a more sanitary alternative to the use of a sponge, washcloth, or other implement intended for extensive reuse, because such implements can develop bacterial growth, unpleasant odors, and other undesirable characteristics related to repeated use.

However, while disposable articles, which can be easily used by young children, are desirable they have their own problems. Retention in the hand of a user of such disposable articles, especially during vigorous scrubbing, is one such problem. If the washcloth is prone to be dropped during use the user is more concerned with retaining the article in hand instead of actually using the article for its intended purpose.

It can now be appreciated that using consumer products involves many aspects for both the child and the caregiver, especially for the child incapable of reading. Some of these aspects affect children differently, or may not even be a factor for a particular child. It is this uniqueness of each individual child that presents a major challenge for both the child and the caregiver. If any of these aspects are unsuccessful, the child's progress in learning how to, for example bathe or clean properly can be unnecessarily delayed due to numerous failures and frustrations. In the past reusable washcloths and sponges have been made in various shapes, such as puppets and with child appealing graphics, in order to make the use of these products fun and enjoyable. However, these reusable products still suffer from the problems associated with repeated use, i.e., bacterial growth, unpleasant odors, and other undesirable characteristics related to extensive reuse. One the other hand, while disposable products side step this problem of extensive reuse, no effort has been made to make disposable products more appealing to children.

The problem remains that there is no disposable articles, products or system available for children of all ages and sizes, which can be easily handled and the method of utilizing easily understood, by the child. The need also remains for disposable cleaning products which are easy to use, appealing to and suitable for use by children, of different ages, all sizes and/or stages of development. Furthermore, the need remains for an article which a child will desire to use and is retained in a user's hand such that the consumer can focus on the task at hand, namely using the product correctly, without having to be concerned with retaining the article in their hand.

SUMMARY OF THE INVENTION

A first aspect of the present invention provides, a disposable child sized article comprising:
   (a) a nonwoven sheet member;
   (b) retaining aid disposed on the nonwoven member, the retaining aid enables a child to retain the nonwoven sheet member on a hand of the child;
   (c) a benefit composition, wherein the nonwoven member is releasably carrying the benefit composition; and
   (d) child graphic disposed on the nonwoven member.

A second aspect of the present invention provides, a disposable child sized article comprising:
   (a) a nonwoven sheet member;
   (b) retaining aid disposed on said nonwoven member, said retaining aid enables a child to retain said nonwoven sheet member on a hand of said child;
   (c) a benefit composition, wherein said nonwoven member is releasably carrying said benefit composition;
   (d) a child graphic disposed on said nonwoven member and
   (e) a usage indicator.

All documents cited are, in relevant part, incorporated herein by reference; the citation of any document is not to be construed as an admission that it is prior art with respect to the present invention. It should be understood that every limit given throughout this specification will include every lower, or higher limit, as the case may be, as if such lower or higher limit was expressly written herein. Every range given throughout this specification will include every narrower range that falls within such broader range, as if such narrower ranges were all expressly written herein. All percentages, ratios and proportions are by weight, and all temperatures are in degrees Celsius (° C.), unless otherwise specified. All measurements are in SI units unless otherwise specified.

BRIEF DESCRIPTION OF THE DRAWINGS

The above-mentioned and other features and objects of this invention and the manner of attaining them will become more apparent, and the invention itself will be better understood by reference to the following description of the invention taken in conjunction with the accompanying drawings, wherein.

DETAILED DESCRIPTION

Figure 1:
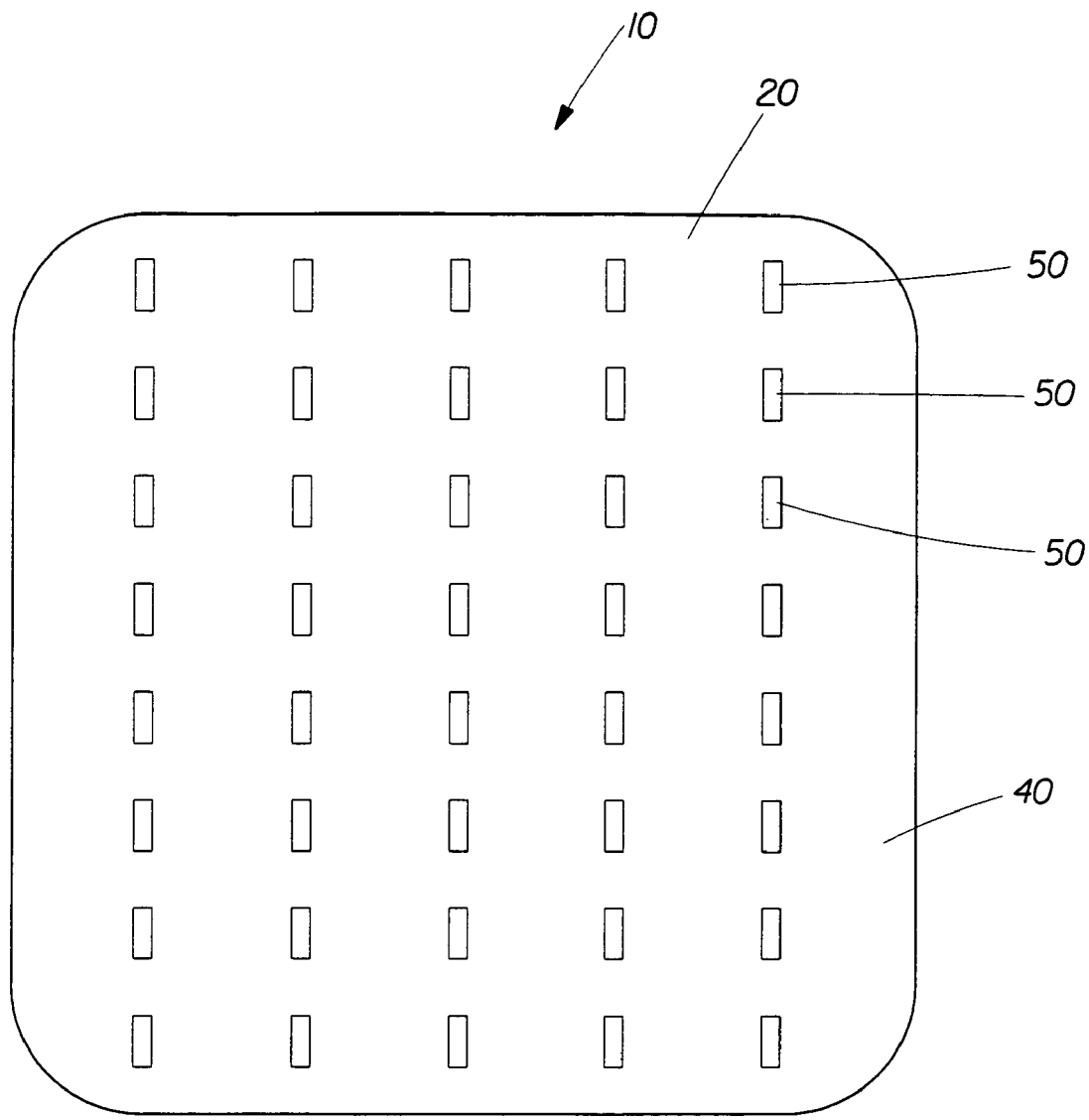
FIG. 1 illustrates one embodiment of a disposable child sized article.

The instant disposable child sized article, and methods of the present invention are suitable for use by children. Due to the ease and simple method of use very young children are able to use the instant articles to an extent independently.

Definitions

As used herein the abbreviation "gsm" means "grams per square meter".

As used herein, "disposable" is used in its ordinary sense to mean an article that is disposed or discarded after a limited number of usage events, preferably about 2 or less, and more preferably about 1 entire usage events.

The term "releasably carrying" means that a composition is contained in and/or on a nonwoven member or parts thereof and is readily releasable from the nonwoven member by application of water and/or application of some force to the nonwoven member, for example, wringing the disposable child sized article, wiping a surface such as but not limited, a child, automobile, tableware, window etc, or immersing part or all of the disposable child sized article in water.

As used herein, the term "comprising" means that the various components, ingredients, or steps, can be conjointly employed in practicing the present invention. Accordingly, the term "comprising" is open-ended and encompasses the more restrictive terms "consisting essentially of" and "consisting of." Other terms may be defined as they are discussed in greater detail herein.

As used herein, the term "graphic" means any design, shape, pattern, or the like that is or becomes visible on an article, and specifically includes text messages, that include one or more alphanumeric symbol, pictorial images that consist of one or more pictures, and combination thereof.

As used herein, the term "child graphic" means any graphic which appeals to a child such that the child will want to possess and/or interact with the disposable child sized article in some fashion, such as the typical use to which the disposable child sized article is put. The child graphic may be aesthetically pleasing, objectively and/or subjectively desirable to any child. The child graphic may in addition be aesthetically pleasing and/or objectively desirable to a child's caregiver. Typically, any child graphic may be supportive and/or encouraging of a child. This support and/or encouragement may be of any suitable subject matter, such as but not limited to, providing advice to the child on any of a range of diverse subjects such as: education, e.g., numbers, letters, words, shapes and the like, child appropriate facts and factoids, and combinations thereof; sports and games; jokes, rhymes, limericks, humorous stories and the like; social and religious issues, such as but not limited to, sharing and caring, bullying, civics, and the like; safety, such as but not limited to, stranger danger, road safety, hygiene, (i.e., hand washing, bottom wiping and the like); and combinations thereof. One such suitable subject matter of the support and/or encouragement can be with respect to the child's desire to possess and/or interact with the disposable child sized article in some fashion.

A child graphic can comprise a character or characters. This character may be shown using the article in an appropriate fashion. The child graphic may additionally include one or more images of the character, characters or parts thereof, performing one or more steps associated with using the disposable child sized article. Illustrative examples of such step(s) include, but are not limited to: preparation step(s) associated with using the article, such as but not limited to accessing the article and the like; lathering the article and the like; using the article; and/or disposing of the spent article and/or optional container and the like.

Without wishing to be limited to the specific embodiments listed, suitable examples of child graphics may include: a character graphic operating a vehicle, and another child graphic comprising stars, balls, or the like; a character graphic jumping rope, and another child graphic comprising flowers; a character graphic feeding or nurturing and animal, and another child graphic comprising letters of the alphabet; a character graphic holding or using a racquet, bat, glove, other sporting equipment, or illustrated on a sporting field, or the like, and another child graphic comprising objects that are not associated with sports, sporting equipment or the like; a character graphic holding a butterfly net or the like and another child graphic comprising objects that are not associated with butterflies or the like; a character graphic holding a fishing pole, sitting in a boat or the like and another child graphic comprising objects that are not associated with fish, inflatable water toys or the like; a character graphic holding flowers, plants, gardening tools or the like and another child graphic comprising objects that are not associated with flowers, plants or gardening; a character graphic comprising a pet or other animal or an anthropomorphous image feeding, training or nurturing an animal and another child graphic comprising objects that are not associated with pets, animals, animal food, pet toys, or the like; a character graphic playing in a specific environment such as a doll house, barn yard or the like and optionally another child graphic; a character graphic holding or using a telescope or the like and another child graphic comprising objects such as stars, planets or the like; a character graphic comprising a racecar and another child graphic associated with racing; a character graphic comprising a submarine and another child graphic comprising objects associated with fish, bubbles, shells or the like; or other suitable graphics.

The child graphic may vary depending upon the age and/or developmental stage of the child. Typically, this would mean when a graphic is intended for a younger child, typically of approximate age 3 or 4, the graphics will be simpler in nature and comprise bright colors, and typically be easily identifiable and relatable to by a child of that age. The selection of available colors as well as the possible complexity of the child graphics may be increased as the age of the intended child increases. Typically, the older the intended child the more colors, especially subtle colors shades etc, and complex images are available for use on the article.

The child graphic may vary depending upon the gender of the intended child; for example, the child graphic may comprise colors and images which are appealing to girls, such as pinks and images of dolls, rabbits, doll houses and the like or the child graphic may comprise colors and images which are appealing to boys, such as blues and rockets, construction machines, trains and the like. Alternatively, the child graphic may comprise colors and images which are gender neutral and are appealing equally to girls and boys such as purples and greens and cartoon characters, or the child graphic may comprise colors and images which comprise parts which are appealing to boys, parts which are appealing to girls and is overall appealing to both boys and girls.

The term "unrelated in subject matter" is used herein to mean that one graphic is not the same as or is not associated with the subject matter of another graphic. The subject matter relationship or lack thereof can be between two or more text messages, between two or more pictorial images, or between a combination of one or more text messages and one or more pictorial images. The term "text message" means a graphic consisting of one or more alphanumeric symbols, and the term "pictorial image" means a graphic consisting of one or more pictures. The terms "text image" and "pictorial image" are mutually exclusive as used herein.

By way of illustration and without wishing to be limited to the enumerated examples, two pictorial images are considered unrelated in subject matter where the images: illustrate items that are neither identical nor different sizes, shapes, or colors of a common object; illustrate two objects that are not commonly associated with one another, such as an animal and a building block, a jump rope and a flower, a car and a star, a letter of the alphabet and a water toy, a fish and an apple, illustrate items used in unrelated activities, such as items used in sporting activities and items used in gardening activities, or other unrelated activities; or the like. Similarly, two text messages are considered unrelated in subject matter where the messages: are neither identical nor jointly form a sentence, thought, or action; refer to two items that are not commonly associated with one another, such as "ball" and "flower," "fish" and "pencil," "car" and "ghost," or other such unrelated words; or the like. Likewise, a text message and a pictorial image are considered to be unrelated in subject matter where the text does not name, define, describe or otherwise relate to the image.

As used herein, the phrase "related in subject matter" refers to the situation where the subject matter of one graphic is the same as or is associated with the subject matter of another graphic. By way of example, two pictorial images are considered related in subject matter where the images are identical; separately illustrate different sizes, shapes, colors of a common object; each illustrate one and the other of two objects that are commonly associated with one another, such as the moon and stars, a body of water and water toys, a sandbox and suitable toys, a baseball bat and ball, a barn and animals, or the like; illustrate different items used in a particular activity, such as a sporting activity, a gardening activity or the like; jointly illustrate geometrically mating or engaging elements such as a triangle and a triangularly-shaped aperture, or two halves of a zipper; each illustrate one part of a multipart picture; or the like. Similarly, two text messages are considered related in subject matter where the messages: are identical; jointly form a sentence, thought, or action such as "jump" and "up"; each refer to one and the other of two items that are commonly associated with one another, such as but not limited to "bat" and "ball; jointly present a question and answer; or the like. Likewise, a text message and a pictorial image are considered to be related in subject matter where the text names, defines or describes the image; or the like.

The term "disposed on" and variations thereof are intended to mean that one element can be integral with another element, or that one element can be a separate structure bonded to or placed with or placed near another element. For example, graphics can be formed or applied directly or indirectly to a surface of a substrate, such as but not limited to, the nonwoven sheet member, any surface of a container, or other variations or combinations thereof. In particular embodiments, graphics may be printed, sprayed, or otherwise applied directly on a layer of the nonwoven sheet member.

Disposable Child Sized Article

Referring to FIG. 1, there is illustrated one possible embodiment of a disposable child sized article 10, in accordance with the present invention. The disposable child sized article 10 comprises a nonwoven sheet member 20 having a first side 40 and second side 60 (FIGS. 2 to 6).

The disposable child sized article 10 also comprises a benefit composition 50. The nonwoven sheet member is releasably carrying the benefit composition 50. In one embodiment of the present invention the benefit composition may be present on a part of the nonwoven sheet member, such as but not limited to, in the form of stripes, spots, geometric patterns, non-geometric patterns or in a random distribution. In an alternative embodiment, the benefit composition 50 may be present on the entire nonwoven sheet member 20 of the disposable child sized article 10. In another an alternative embodiment, not shown, the benefit composition may be present in the interior of the nonwoven sheet member 20 of the disposable child sized article, and/or on the surface of the nonwoven sheet member 20. The benefit composition 50 may be carried on any surface, and/or interior of the nonwoven sheet member as long as the nonwoven sheet member 20 is releasably carrying it. The benefit composition, such as but not limited to, type, components, amount and the like, is explained in more detail herein.

The material of which disposable child sized article are made from should be strong enough to resist tearing during normal use, yet still provide softness to the child's tender skin. In embodiments that require the article to contact water, the material should be water insoluble, or at least capable of retaining its form for the duration of the child's use experience.

The disposable child sized article may be subjected to various treatments, such as but not limited to, physical treatment, such as zone activation, ring rolling SELFing and the like; chemical treatment, such as rendering part or all of the disposable child sized article hydrophobic, and/or hydrophilic, and the like; thermal treatment, such as softening of fibers by heating, thermal bonding and the like; and combinations thereof.

The disposable child sized article may be of any size which is suitable for use by a child. Furthermore, the article may be of a size to be used by a specific developmental age of child, such as 4, or 7 and the like. Alternatively, the disposable child sized article may be of a size which is suitable for use by any child. Typically, the size of the disposable child sized article will depend upon many factors such as dexterity and hand eye coordination of the child, size of the child's hand, gender, ethnicity, and the like. Anthropomorphic data on child hand sizes may be found in Consumer Safety CHILDATA: Handbook of Child Measurements (Beverly Norris & John Wilson, June 1985). Furthermore, the dimensions and size of the disposable child sized article will depend upon the shape, weight and composition of the nonwoven sheet member, the retaining aid used and the intended use of the article. Typically, a substantially rectangular disposable child sized article will have a length of from about 50 mm to about 200 mm, a width of from about 50 mm to about 150 mm and a thickness of about 0.01 mm to about 30 mm. Alternatively, the area of one side of the disposable child sized article, such as but not limited to the side comprising the benefit composition, has an area of from about 100 $mm^2$ to about 30,000 $mm^2$.

The disposable child sized article may also optionally comprise a usage indicator. This optional usage indicator provides a means for the child to readily identify correct usage of the article, when all or a portion benefit composition has been released from the nonwoven member, and/or they have used the article for a sufficient amount of time. The usage indicator may be a separate feature or it may be part of the benefit composition, or it may be a part of a child graphic, or a child graphic when more than one child graphic is present. This type of usage indicator is described further herein. Other suitable usage indicators include, but are not limited to, pH (e.g., at a specific pH or pH range a noticeable event occurs such as color change, noise generation or cessation and the like and combinations thereof), temperature (e.g., the article may feel warm cold for its intended use and then revert to ambient temperature, or change temperature form ambient after a period of time), time (e.g., the indicator may change size shape, color etc after a time period since it was exposed to water air, oxygen, shear or other force and the like), and the like and combinations thereof. In one optional embodiment the usage indicator provides a visual signal during use of the article at least a portion of the benefit composition has been released from the nonwoven member.

When present, the type of optional usage indicator will depend upon many factors, such as but not limited to, size and type of material present in article and nonwoven member, benefit composition, intended use of the article, age of child using the article the child graphic used and the like. In any event the selection of the usage indicator, when present, should not typically not be in isolation from the other elements, such as but not limited to, any character graphic, for example a usage indicator which changes to red, is probably not suitable for younger children because of the possible distress it may possibly cause to a care giver, who thinks the child is possibly hurt, and/or to the child who may think the character is possibly hurt, or a use indictor which changes to green may possibly appear to be gross and slimy to care givers and/or girls (but which may conversely possibly be fascinating and very appealing to boys). In any event selection of usage indicator will depend upon many factors and should not typically be made in isolation of the other components of the article.

Nonwoven Sheet Member

In one embodiment of the instant invention, the nonwoven sheet member comprises a mixture of natural fibers and synthetic fibers. In alternative embodiments of the present invention the nonwoven sheet member may wholly comprise natural fibers, while in other alternative embodiments still may wholly comprise synthetic fibers.

Suitable natural fibers include, but are not limited to, cellulosic fibers, such as wood pulp fibers, cotton, and rayon. Suitable synthetic fibers include manmade fibers commonly used in textiles. In one preferred embodiment the fibers comprise, at least one polymer selected from the group consisting of polyolefin (e.g., polyethylene, polypropylene, etc.) polyesters, polyether (e.g., PET, etc.) cellulose, rayon, polyamide, polyvinyl alcohol, and polyacrylic. It is also possible to use bicomponent polymers, or simply bico or sheath polymers. These bico polymers can be used as a component fiber of the nonwoven sheet member, and/or they may be present to act as a binder for the other fibers present in the nonwoven material. Suitable nonwovens with good softness include, but are not limited to, nonwoven materials comprising polypropylene, polyethylene, cellulose, rayon, polyether, PET, bicomponent polymers, and combinations thereof.

Various forming methods can be used to form the nonwoven sheet members. For instance, the disposable child sized article can be made by nonwoven dry forming techniques, such as air-laying, or alternatively by wet laying, such as on a papermaking machine, of a continuous web out of which the cleansers are made. Other nonwoven manufacturing techniques, including but not limited to, techniques such as adhesive bonding, melt blown, spunbonded, carding, needle punched, hydroentanglement and lamination methods may also be used.

In one alternative optional embodiment the nonwoven member is selected from the group consisting of air laid nonwovens, wet laid nonwovens, spunbonded nonwovens, hydroentangled nonwovens, carded nonwovens melt blown nonwovens, coformed nonwovens, and combinations thereof. The nonwoven sheet members of the present invention may be subjected to various treatments, such as but not limited to, physical treatment, such as zone activation, ring rolling SELFing and the like; chemical treatment, such as rendering part or all of the disposable cleaning implements hydrophobic, and/or hydrophilic, and the like; thermal treatment, such as softening of fibers by heating, thermal bonding and the like; and combinations thereof.

It is also within the scope of the present invention that the nonwoven sheet member when may comprise laminates of two or more substrates or webs, such as but not limited to a two-layer or three-layer laminate. Commercially available laminates, or purpose built ones would be within the scope of the present invention. Additionally, the nonwoven sheet member, may be flat or textured. The formation of textured nonwoven sheet member and laminates forms no part of this invention.

In one embodiment of the present invention the surface of nonwoven sheet member is essentially flat. In another embodiment of the present invention the surface of the nonwoven sheet member may optionally contain raised and/or lowered portions. These can be in the form of logos, indicia, trademarks, geometric patterns, images of the surfaces that the disposable child sized article is intended to clean (i.e., child's body, face, toys, floors, automobiles, walls, etc.). They may be randomly arranged on the nonwoven sheet member or be in a repetitive pattern of some form. They may be on one or both of the sides or surfaces of the nonwoven sheet member. In one embodiment one of the nonwoven sheet members contains a repetitive pattern or alternating raised and lowered portions of the substrate. This variation in or on the surface of one side of the nonwoven sheet member may be included to, for example, convey to the child or a caregiver information on the disposable child sized article intended use, how a child is to use the retaining aid, which brand or type of disposable child sized article they are using or even to aid in cleaning of a surface, such as the child's body, child's hair, kitchen counter top, an automobile, etc.

In another embodiment of the present invention, the nonwoven sheet member may be biodegradable. For example, the nonwoven sheet member may be made from a biodegradable material, such as a polyesteramide.

Additional information on materials which are suitable for use as the disposable child sized article, nonwoven sheet members, retaining aids and/or other components thereof can be found in the following patents: U.S. Pat. No. 3,862,472 issued Jan. 28, 1975; U.S. Pat. No. 3,982,302 issued Sep. 28, 1976; U.S. Pat. No. 4,004,323 issued Jan. 25, 1977; U.S. Pat. No. 4,057,669 issued Nov. 8, 1977; U.S. Pat. No. 4,097,965 issued Jul. 4, 1978; U.S. Pat. No. 4,176,427 issued Dec. 4, 1979; U.S. Pat. No. 4,130,915 issued Dec. 26, 1978; U.S. Pat. No. 4,135,024 issued Jan. 16, 1979; U.S. Pat. No. 4,189,896 issued Feb. 26, 1980; U.S. Pat. No. 4,207,367 issued Jun. 10, 1980; U.S. Pat. No. 4,296,161 issued Oct. 20, 1981; U.S. Pat. No. 4,309,469 issued Jan. 25, 1982; U.S. Pat. No. 4,682,942 issued Jul. 28, 1987; U.S. Pat. Nos. 4,637,859; 5,223,096; 5,240,562; 5,556,509; and 5,580,423 and U.S. Patent Application No. US2003/0217425 published on Nov. 27, 2003 and filed on May 23, 2002 by Datta et al.

Additional information on suitable disposable child sized article, nonwoven sheet members and/or retaining aids may be found in copending U.S. Provisional Patent Application Nos. 60/453,160 filed on Mar. 10, 2003, entitled "Disposable Nonwoven Cleansing Mitt" in the name of Dobrin et al; 60/453,166 filed on Mar. 10, 2003, entitled "Disposable Nonwoven Cleansing Mitt" in the name of Benjamin et al; and 60/453,167 filed on Mar. 10, 2003, entitled "Child's Cleansing System" in the name of Sanchez et al.

The manufacture of disposable child sized article, retaining aid, nonwoven sheet member and components thereof, such as, nonwoven sheet substrate per se forms no part of this invention.

Retaining Aid

The disposable child sized article of the present invention may comprise a retaining aid which enables a child to retain the nonwoven sheet member on a hand of the child. The retaining aid may be anything suitable for permitting a removable attachment of the disposable child sized article of the present invention to a child's hand. Suitable retaining aids, include but are not limited to, hook and loop fasteners such as Velcro® and the like, elastic members, buttons, fasteners, tabs, resealable tape, belts, clips, refastenable adhesives, and combinations thereof.

In an alternative embodiment of the present invention, the retaining aid is selected such that it will adhere, cling or stick to the child's hand prior to and during use. For example, the disposable child sized article 10 of FIG. 2, may optionally comprise as the retaining aid material that will adhere, stick or cling to the child's hand prior to and during use. This optional adhesion may be achieved in a variety of ways, including but not limited to, adhesive, friction, electrostatic attraction, conformation or constriction of the retaining aid or a portion thereof, to the shape of the child's hand when wet, fluid between the child's hand and the retaining aid and combinations thereof. Suitable material for this alternative optional embodiment of the retaining aid, include but are not limited to, adhesive, polyolefin films such as films comprising polyethylene and/or polypropylene, and combinations thereof.

The retaining aid may be attached to the nonwoven sheet member 20 in any suitable fashion including, but not limited to, ultrasonically bonding, sewing, adhesive or glue, mechanically bonding, fusion bonding, heat or thermal bonding and combinations thereof.

The retaining aid may be of any suitable shape and/or size and will depend upon may factors such as, but not limited to, size of the disposable child sized article, the dry weight of the disposable child sized article, the wet weight of the disposable child sized article, material used in the disposable child sized article, benefit composition present, retaining aid used, and the like and combinations thereof.

FIGS. 2 to 6 illustrate some non-limiting examples of some suitable retaining aids present on the second side 60 of the nonwoven sheet member 20.

Figure 2:
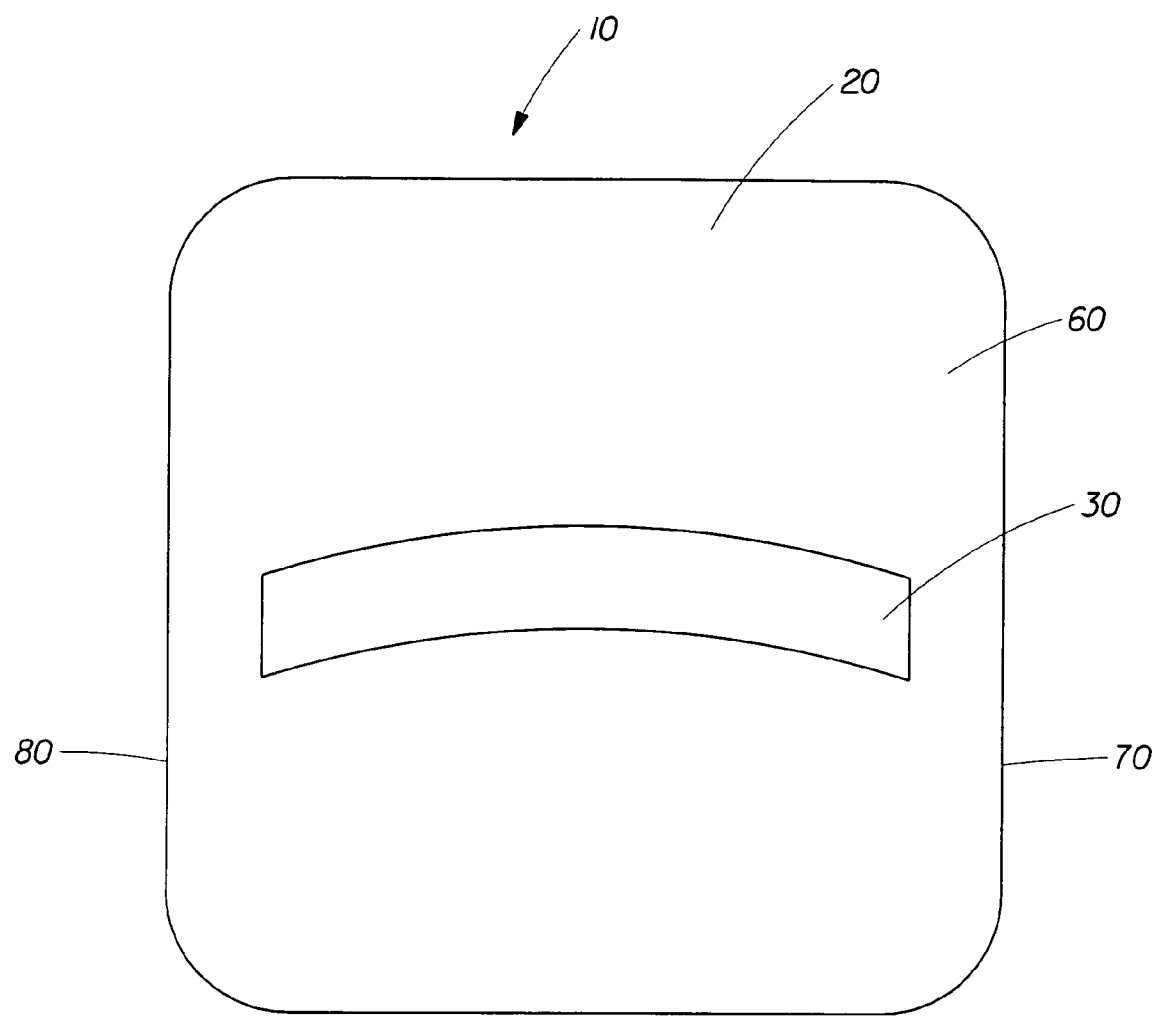
FIG. 2 illustrates one possible embodiment of the reverse side of the disposable child sized article of FIG. 1.

In FIG. 2, the retaining aid 30 is attached to the second side 60 of the nonwoven sheet member 20 so it is inboard of and approximately perpendicular to the sides 70 and 80 of the nonwoven sheet member 20.

Figure 3:
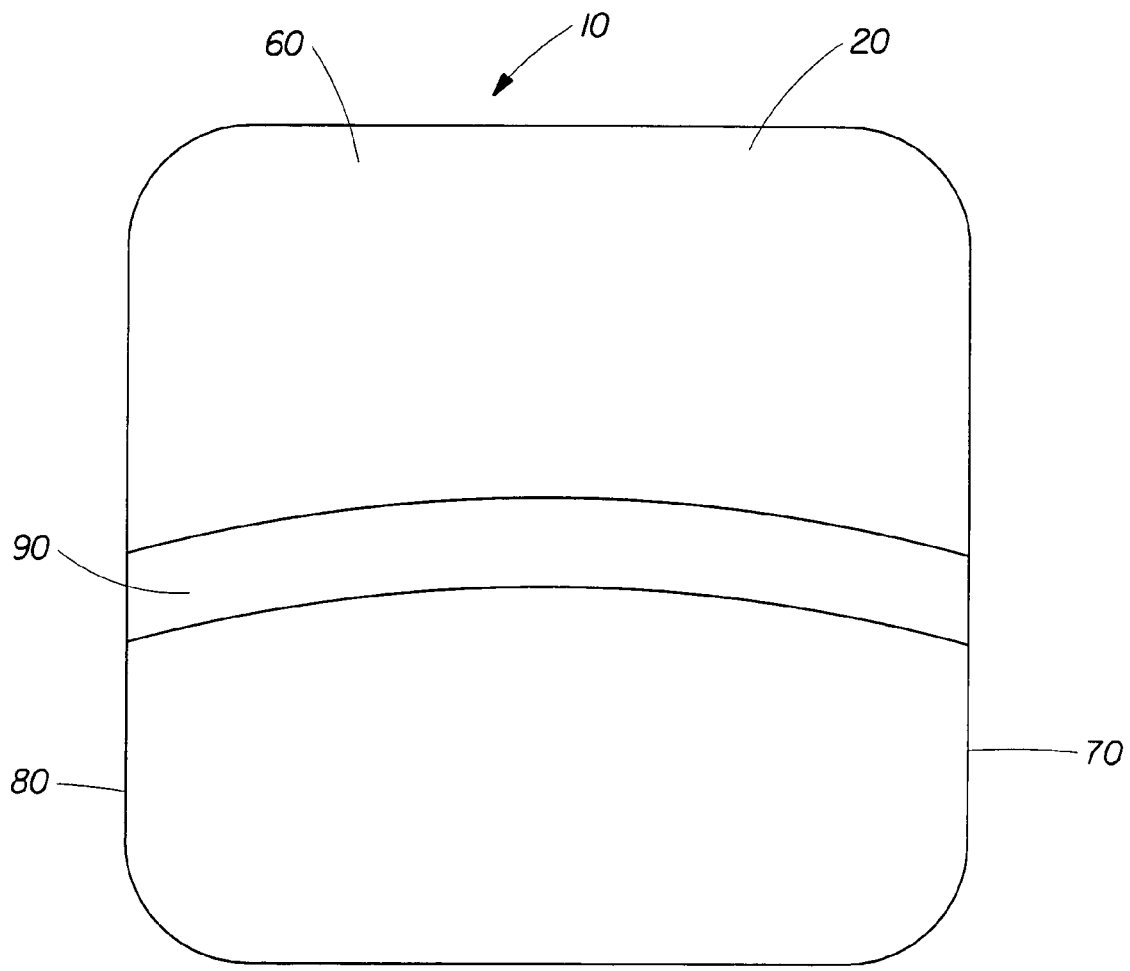
FIG. 3 illustrates another alternative embodiment of the reverse side of the disposable child sized article of FIG. 1.

In FIG. 3, the retaining aid 90 is attached to the second side 60 of the nonwoven sheet member 20 at approximately the sides 70 and 80 and is also approximately perpendicular to the sides 70 and 80 of the nonwoven sheet member 20.

Figure 4:
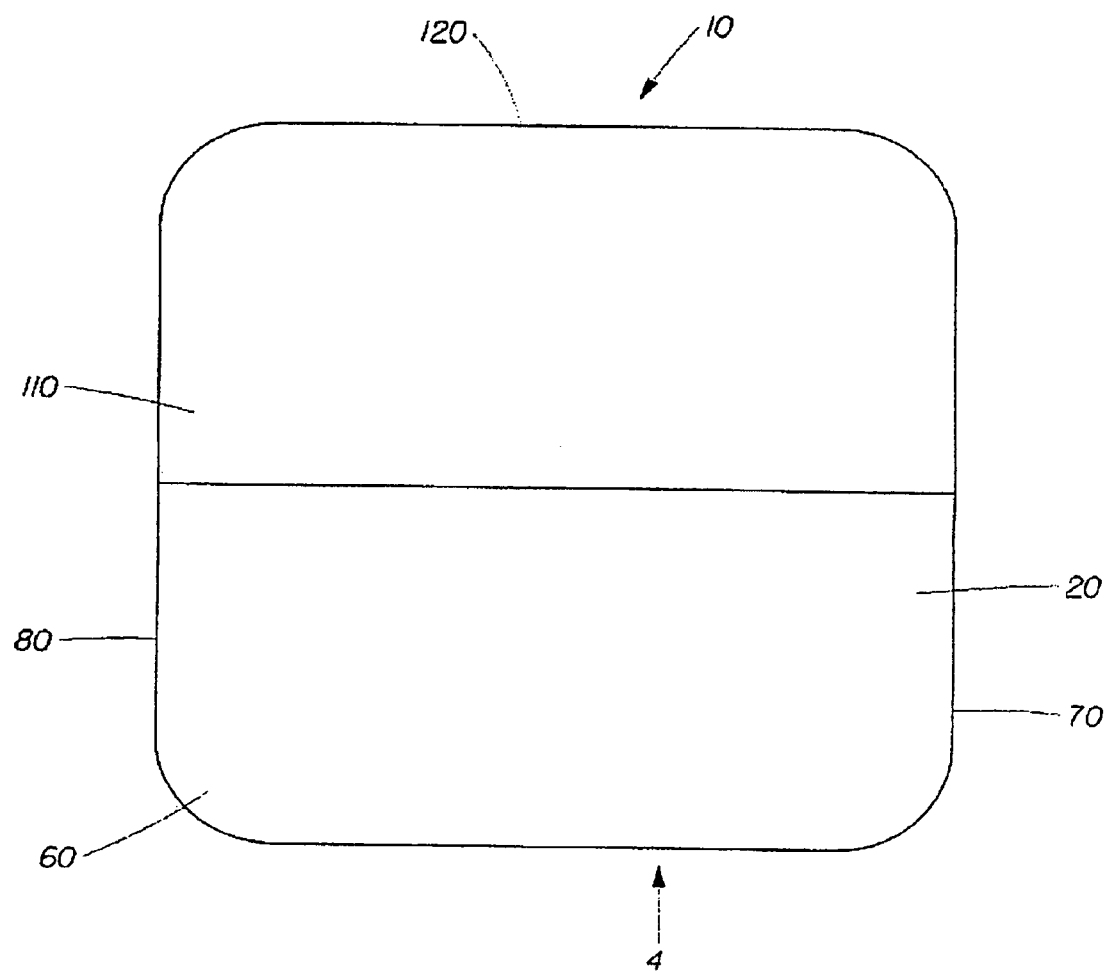
FIG. 4 illustrates another alternative embodiment of the reverse side of the disposable child sized article of FIG. 1.
Figure 5:
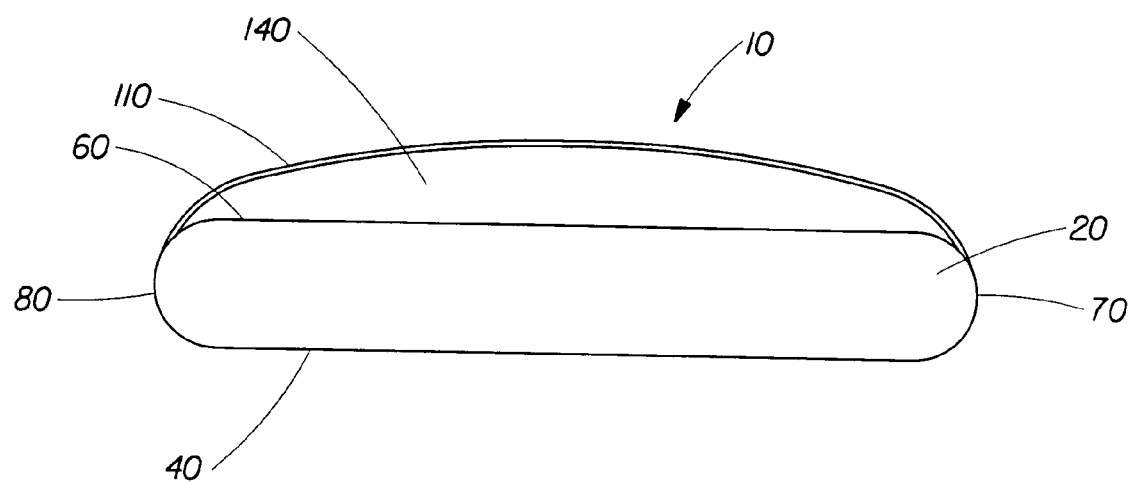
FIG. 5 illustrates an end view in the direction of arrow 4 of the disposable child sized article of FIG. 4.

FIGS. 4 and 5 illustrate yet another alternative suitable retaining aid which may be present on the second side 60 of the nonwoven sheet member 20. The retaining aid 110 is joined to the sides 70 and 80 and the top 120 of the nonwoven sheet member 20. thereby forming a pocket 140 in which the child's hand, or part thereof is placed. In one optional embodiment the retaining aid 110 is typically approximately three quarters the length or less, preferably approximately about ⅓ to about ¼ the length of the nonwoven sheet member 20. In an unillustrated alternative embodiment, the retaining aid 110 may be additionally joined to the nonwoven sheet member 20 at one or more points between the sides 70 and 80 thereby dividing the pocket 140 into two or more portions. These portions may be of equal or different volume and may be intended to which at least a portion of the child's hand is placed.

Nothing in this disclosure either express or implied should be construed in any manner as limiting the retaining aid 110 to the second side 60 of the nonwoven sheet member 20. The retaining aid 110 may be present on the first side 40 of the nonwoven sheet member 20 or any suitable surface of the nonwoven sheet member 20.

Figure 6:
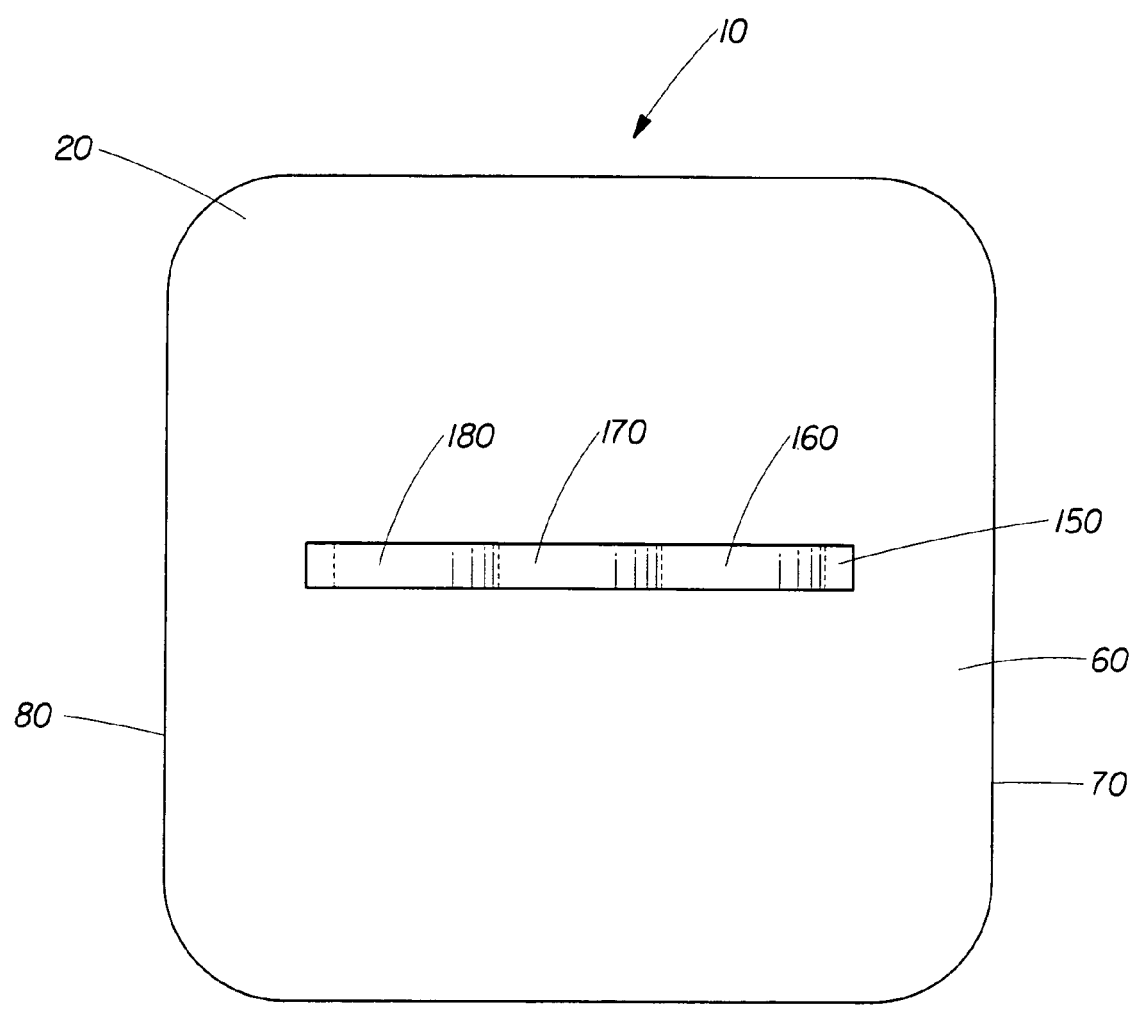
FIG. 6 illustrates another alternative embodiment of the reverse side of the disposable child sized article of FIG. 1.

FIG. 6 illustrates another alternative embodiment of the present invention where the retaining aid 150 comprises three half loops or arches 160, 170 and 180 through which three digits of a child's hand are placed. The arches 160, 170 and 180 may comprises three discrete elements and may be individually attached to the nonwoven sheet member 20, or alternatively joined together and the attached to the nonwoven sheet member 20. Alternatively, the arches 160, 170 and 180 may comprise a single piece of material and the attachment of the material to the nonwoven sheet member 20 is in such a fashion as to form the arches 160, 170 and 180. While the arches 160, 170 and 180 are shown in FIG. 6, it is within the scope of the present invention to use more or less arches, for example two, four or five instead of three. Similarly, while the arches 160, 170 and 180 are each illustrated in FIG. 6 as in physical contact with another arch, it is within the scope of the present invention to use arches which are not in contact or use arches where some are in physical contact and some are not.

Figure 7:
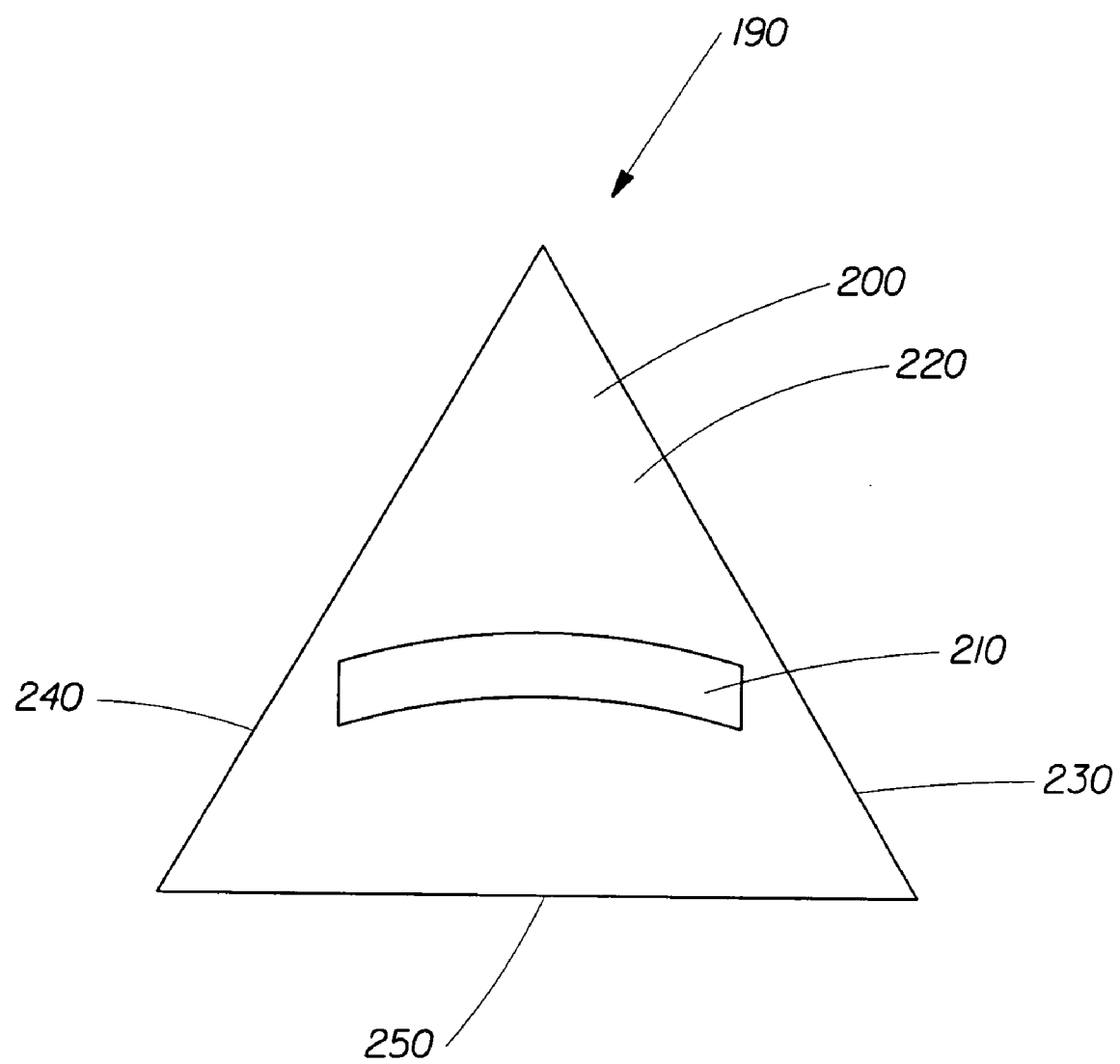
FIG. 7 Illustrates another alternative embodiment of a disposable child sized article.
Figure 8:
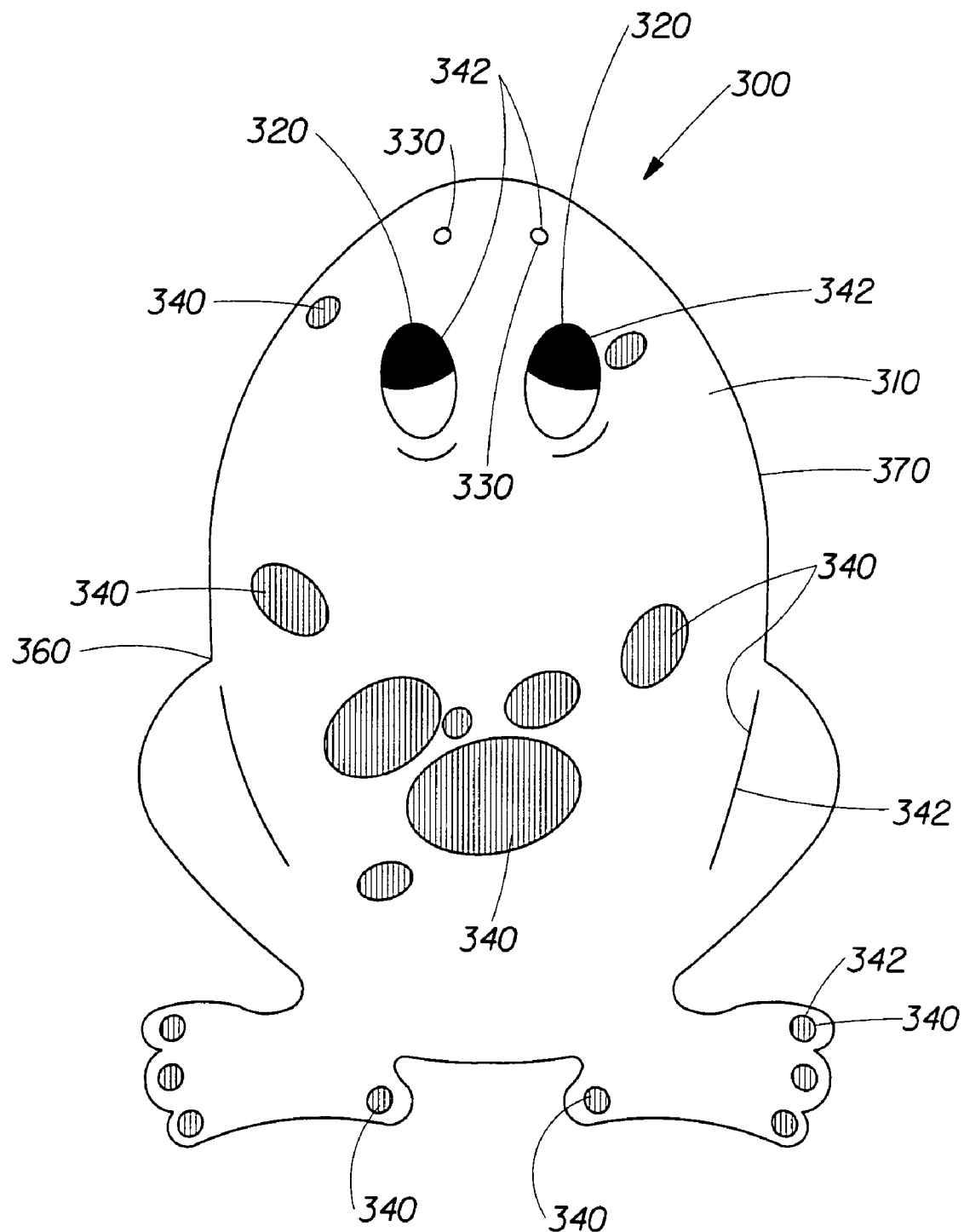
FIG. 8 illustrates another alternative embodiment of a disposable child sized article.

FIG. 7 illustrates a disposable child sized article 190 comprising a nonwoven sheet member 200 releasably containing a benefit composition and having a first side 220 and a retaining aid 210. The retaining aid 210 is attached to the first side 220 of the nonwoven sheet member 200 so it is inboard of the sides 230 and 240 and approximately parallel to the bottom 250 of the nonwoven sheet member 190.

The disposable child sized article 190 of FIG. 7 is triangular in shape, whereas the disposable child sized article 10 of FIGS. 1 to 6 is approximately rectangular in shape. The disposable child sized article as well as the nonwoven sheet member and the retaining aid may be or any suitable size and shape, such as but not limited to square, rectangular, triangular, circular, or irregular and the like. The disposable child sized article may be in the form of the object that it is intended to clean such as but not limited to a an automobile, a child, etc. Alternatively, the disposable child sized article may be in the shape of an object which is recognizable to a child, such as an animal, an automobile, a rocket and the like. Examples of this alternative form of the disposable child sized article are illustrated by the disposable child sized article of FIGS. 8 to 11.

FIGS. 8 to 11 illustrate a disposable child sized article 300 where the article is in the shape of an amphibian such as a frog or a toad. The disposable child sized article 300 comprises a nonwoven sheet member 310 which has disposed thereon amphibious markings 342, such as eyes 320, nostril 330, skin markings 340 and the like, to make the disposable child sized article 300 appear more amphibious, i.e. for frog or toad like in appearance to a child. In one optional embodiment of the present invention part or all of the amphibious markings 342 may comprise the benefit composition. In this optional embodiment the amphibious markings 342 would at least fade, more preferably disappear over use and provide a caregiver an easy to use system for identifying if the child has been using the disposable child sized article 300.

Figure 9:
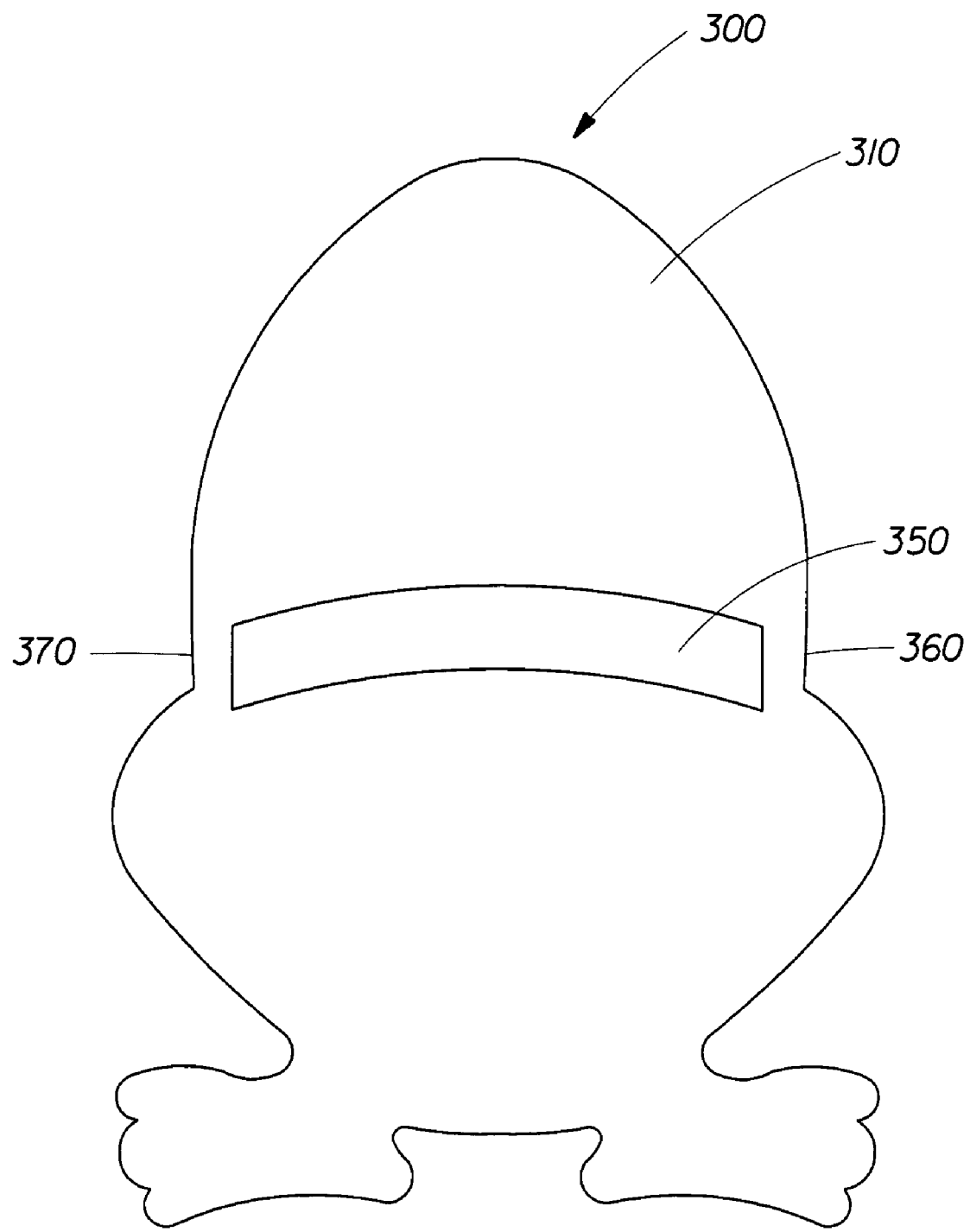
FIG. 9 illustrates one possible embodiment of the reverse side of the disposable child sized article of FIG. 8.

FIG. 9 illustrates one possible retaining aid 350 which is attached on the side of the disposable child sized article 300 without the amphibious markings 342 at approximately the sides 360 and 370 of the disposable child sized article 300.

Figure 10:
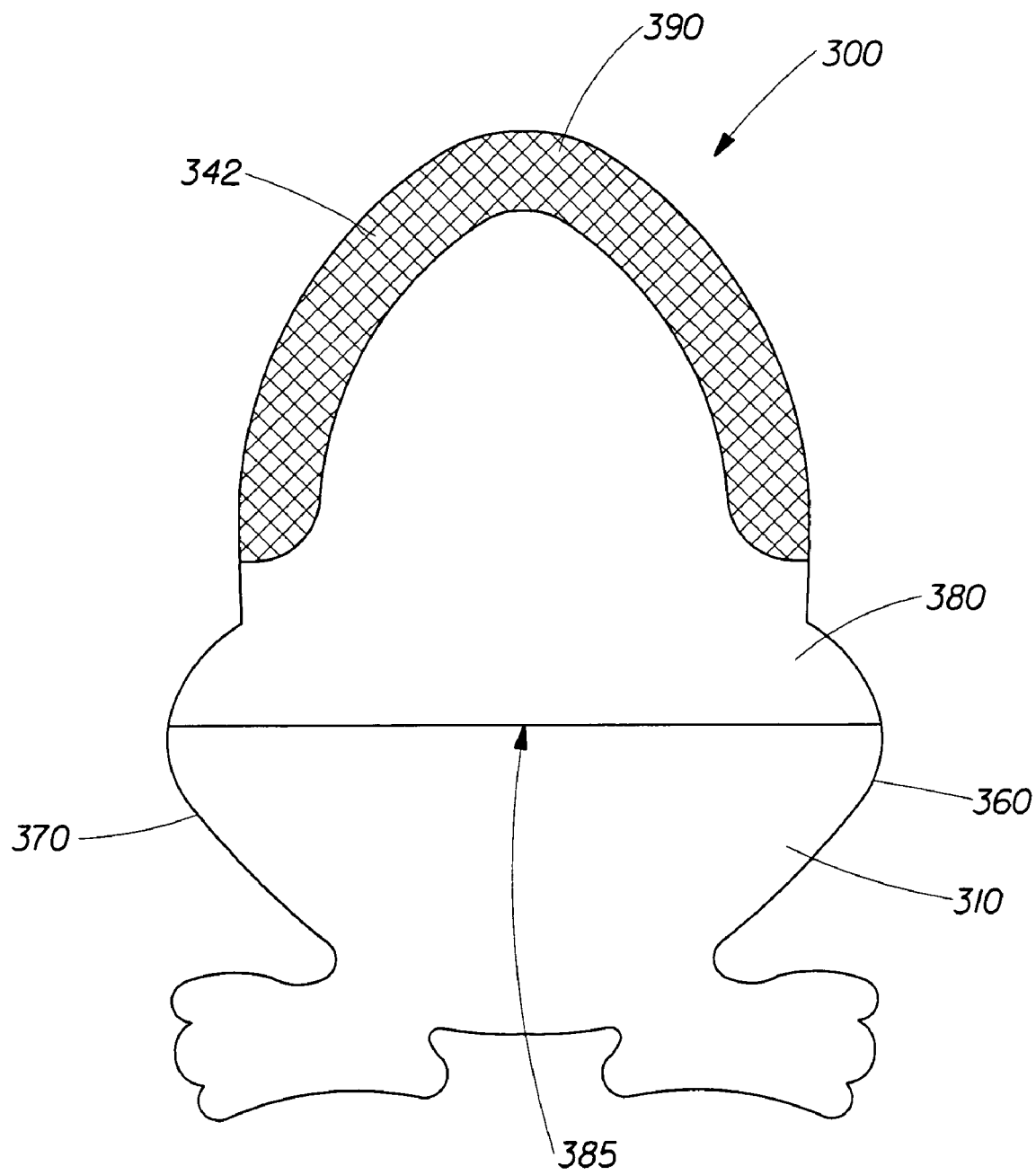
FIG. 10 illustrates another alternative embodiment of the reverse side of the disposable child sized article of FIG. 8.
Figure 11:
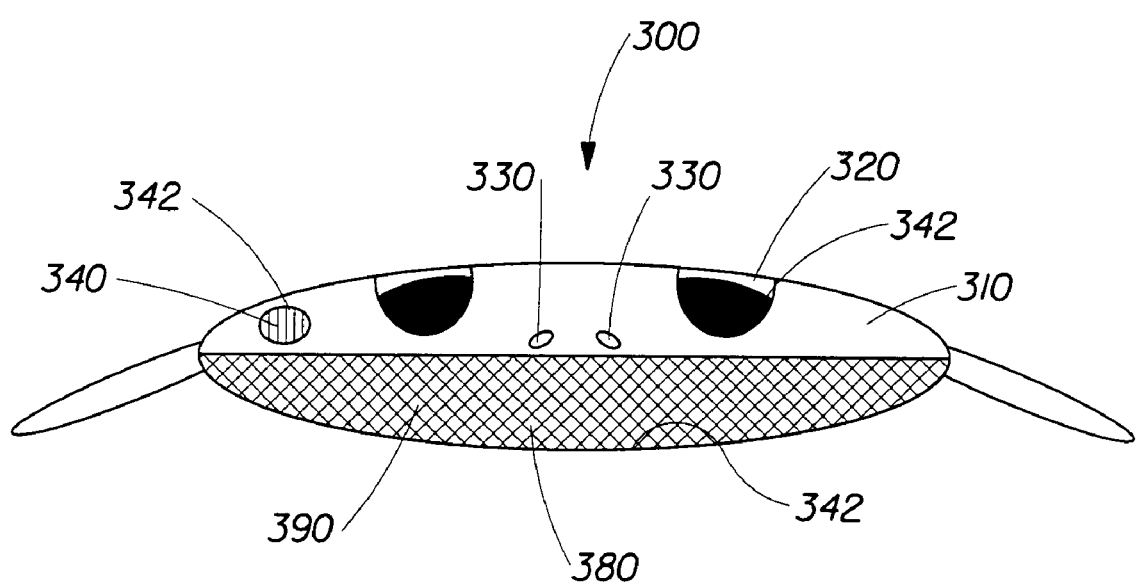
FIG. 11 illustrates an end view in the direction of arrow 6 of the disposable child sized article of FIG. 10.

FIGS. 10 and 11 illustrate another retaining aid 380 which together with the nonwoven sheet member 310 forms a disposable child sized article 300 which appears to be an amphibian puppet, such as a frog, or toad or similar amphibian. The retaining aid 380 is attached to the nonwoven sheet member 310 forming a pocket 385 in a fashion similar to that previously illustrated in FIGS. 4 and 5. The amphibious markings 342 include in this embodiment a section of the nonwoven sheet member 310 and/or the retaining aid 380 which is colored in a fashion so as to resemble an amphibian's mouth 390. In an unillustrated alternative embodiment the retaining aid 380 may be additionally joined to the nonwoven sheet member 310 at one or more points between the sides 360 and 370 thereby dividing the pocket 385 into two or more portions. These portions may be of equal or different volume and may be intended to which at least a portion of the child's hand is placed.

Alternatively, one or more of the amphibious markings 342 may comprise the optional usage indictor, which for example may change color disappear, or appear to generate slime (while not wanting to be limited by theory this is typically believed to be appealing to boys) or the like, or combinations thereof.

To use the disposable child sized article as illustrated in FIGS. 2 to 11 the child's hand, or part thereof is placed between the side of the nonwoven sheet member to which the retaining aid is attached and the retaining aid. In one preferred embodiment the side of the child's hand facing the nonwoven sheet member is the palm side of the child's hand.

Benefit Compositions

The benefit care compositions releasably carried by the disposable child sized article of the present invention may comprise a variety of components such as are conventionally used in benefit compositions. These benefit compositions and the components thereof should be suitable for application to or use by a child; that is, when incorporated into the disposable child sized article of the present invention they are suitable for use in contact with human skin without undue toxicity, incompatibility, irritation, instability, allergic response, and the like, within the scope of sound medical or formulator's judgment.

In one optional embodiment of the present invention the benefit composition may be any composition which is typically used by consumers, such as but not limited to cleaning compositions, moisturizing compositions, medicinal compositions, cosmetic compositions, automotive cleaning compositions, personal cleansing compositions, polishing compositions, germicidal compositions, wax compositions, perfume compositions, dishwashing compositions, hard surface cleaning compositions, glass cleaning compositions, wood cleaning compositions and combinations thereof.

In one embodiment of the present invention the benefit compositions are in the form of a paste, powder, or a dry solid. While benefit compositions comprising more than about 50% by weight of the composition of a liquid carrier, such as water, are within the scope of the present invention, it is preferred that any disposable child sized article be mostly dry, more preferably dry to the touch, prior to contact with the washing environment, that is, until the child first immerses the disposable child sized article or otherwise contacts it with an aqueous liquid, such as, water. Typically, this translates into levels of liquid carrier, such as water (not including water of hydration or water similarly bound by the nonwoven sheet material and/or the components of the benefit composition), of less than or equal to about 10%, more preferably less than or equal to about 7% by weight of benefit composition.

In one alternative embodiment of the present invention the amount of benefit composition present in the disposable child sized article is preferably present in amounts from about 1 gsm to about 200 gsm, more preferably from about 10 gsm to about 175 gsm, even more preferably still from about 20 gsm to about 150 gsm. (Grams of benefit composition per square meter of nonwoven sheet member) Alternatively, each disposable child sized article may preferably contain from about 0.5 g to about 20 g, more preferably from about 1 g to about 15 g of benefit composition per disposable child sized article.

The benefit compositions used in the present invention may contain one or more suitable components. Illustrative, but nonlimiting examples of suitable components of the benefit composition include: surfactant, such as, anionic surfactants, amphoteric surfactants, nonionic surfactants, zwitterionic surfactants, cationic surfactants, and mixtures thereof; enzymes; absorbents; aesthetic components; fragrances; pigments; colorings; colorants; essential oils; skin sensates; anti-acne agents (e.g., resorcinol, sulfur, salicylic acid, erythromycin, zinc, etc.); anti-caking agents; antifoaming agents; preservative; conditioners; hair conditioners; dye; antimicrobial agents (e.g., quaternium-15, paraben preservatives such as but not limited to ethyl paraben, DMDM hydantoin, iodopropyl butylcarbamate (IPBC, etc.); glycerin; binders; buffering agents; bulking agents; chelating agents (e.g., EDTA, etc.); solvents; cosmetic biocides; denaturants; external analgesics; film formers or materials, e.g., polymers, for aiding the film-forming properties and substantivity of the composition (e.g., copolymer of eicosene and vinyl pyrrolidone); humectants; polydimethylsiloxanes (such as, but not limited to, dimethicones); Cyclic polyalkylsiloxanes; opacifying agents; pH adjusters; process aids; reducing agents; sequestrants; skin-conditioning agents; moisturizers; skin soothing and/or healing agents (e.g., panthenol and derivatives (e.g., ethyl panthenol); flavonoids (e.g., bioflavonoids, flavones, isoflavones, etc.); conditioners (e.g., hair conditioners); hair detanglers; skin treating agents; thickeners (e.g., polymeric thickeners, gums, etc.); hydrocolloids; zeolites; sugar amines also known as Amino sugars (e.g., glucosamine, N-acetyl glucosamine, mannosamine, N-acetyl mannosamine, galactosamine, N-acetyl galactosamine, their isomers (e.g., stereoisomers), and their salts (e.g., HCl salt)); phytosterols (e.g., β-sitosterol, campesterol, and the like); oxidants/radical scavengers (such as ascorbic acid (vitamin C), ascorbyl esters of fatty acids, ascorbic acid derivatives (e.g., magnesium ascorbyl phosphate); tea extracts (such as green tea extracts); plant and fruit extracts (e.g., grape skin/seed extracts, melanin, and rosemary extracts, Manjistha, Guggal, kola extract, chamomile, red clover extract, sea whip extract); caffeine; candelilla wax; alpha-bisabolol; aloe vera; allantoin; glycyrrhetic acid; glycyrrhizic acid; abrasives; astringents (e.g., clove oil, menthol, camphor, eucalyptus oil, eugenol, menthyl lactate, witch hazel distillate); gelling agents; thixatropic agents; bulking agents; cosmetic astringents; denaturants; reducing agents; sequestrants; skin bleaching and lightening agents (e.g., hydroquinone); skin treating agents; sunscreen actives (e.g., p-aminobenzoic acid, 2-ethylhexyl-p-methoxycinnamate, 2,2'-dihydroxy4,4'-dimethoxybenzophenone, zinc oxide, titanium dioxide, etc.); and vitamins and derivatives thereof (e.g., tocopherol, tocopherol acetate, beta carotene, nicotinic acid, retinoic acid, retinol, retinoids, retinyl palmitate, niacin, pantothenic, niacinamide, nicotinyl alcohol, and the like); and the like and combinations thereof. The benefit compositions releasably contained by the disposable child sized article may include carrier components such as are known in the art, for example water, alcohols, polyols, and the like. Such carriers can include one or more compatible liquid or solid filler diluents or vehicles which are suitable for application on to and/or use by a child. Alternatively, these carriers may be present in the benefit composition during formulation and application to the nonwoven member and subsequently removed, by any conventional means, such as but not limited to heating, reducing air pressure, and the like.

Some nonlimiting examples of suitable surfactants include ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium monolauryl phosphate, sodium cocoglyceryl ether sulfonate, sodium $C_9$-$C_{22}$ soap, amine oxides such as lauramine oxide and cocoamine oxide, decyl polyglucose, lauryl polyglucose, sucrose cocoate, $C_{12-14}$ glucosamides, sucrose laurate, fatty amines, di-fatty quaternary amines, tri-fatty quaternary amines, imidazolinium quaternary amines, PEG 80 Sorbitan laurate, PEG-150 distearate, sodium laureth-13 carboxylate, disodium lauroamphodiacetate, sodium lauroamphoacetate, cetyl dimethyl betaine, cocoamidopropyl betaine, cocoamidopropyl hydroxy sultaine, and combinations thereof.

Additional information on suitable benefit compositions and possible components thereof may be found in: *CTFA Cosmetic Ingredient Handbook*, Second Edition (1992); *CTFA International Cosmetic Ingredient Dictionary*, Fifth Edition, 1993; McCutcheon's, *Detergents and Emulsifiers*, North American edition (1986), published by Allured Publishing Corporation; McCutcheon's, *Functional Materials*, North American Edition (1992); Sagarin, et al., *Cosmetics Science and Technology* (1972); U.S. Pat. No. 3,929,678, to Laughlin et al., issued Dec. 30, 1975; U.S. Pat. No. 5,833,998 issued to Biedermann et al., on Nov. 10, 1998; U.S. Pat. No. 5,939,082 issued to Oblong et al., on Aug. 17, 1999; U.S. Pat. No. 3,755,560, issued Aug. 28, 1973, to Dickert et al.; U.S. Pat. No. 4,421,769, issued Dec. 20, 1983, to Dixon et al.; U.S. Pat. No. 4,960,764, to Figueroa, Jr. et al., issued Oct. 2, 1990; U.S. Pat. No. 6,335,312 issued on Jan. 1, 2002 to Coffindaffer et al.; U.S. Pat. No. 5,607,980, issued to McAtee et al., on Mar. 4, 1997; U.S. Pat. No. 5,487,884, issued Jan. 30, 1996 to Bissett et al.; U.S. Pat. No. 5,686,082, issued to N'Guyen on Nov. 1, 1997; U.S. Pat. No. 2,831,854, issued to Tucker et al., on Apr. 22, 1958; U.S. Pat. No. 4,005,196, to Jandacek, issued Jan. 25, 1977; U.S. Pat. No. 4,005,195, to Jandacek, issued Jan. 25, 1977; U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al., issued Jun. 15, 1976; U.S. Pat. No. 4,518,772, to Volpenhein, issued May 21, 1985; U.S. Pat. No. 4,517,360, to Volpenhein, issued May 21, 1985; U.S. Pat. No. 4,976,953, to Orr et al., issued Dec. 11, 1990; U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al., issued Dec. 9, 1986; U.S. Pat. No. 4,599,379 to Flesher et al., issued Jul. 8, 1986; U.S. Pat. No. 6,200,554, issued to Yeoh et al., on Mar. 13, 2001; U.S. Pat. No. 6,248,317 issued to Snyder et al., on Jun. 19, 2001; U.S. Pat. No. 4,741,855 issued to Grote et al., on May 3, 1988 and re issued as U.S. RE 34584 on Apr. 12, 1994; U.S. Pat. No. 6,280,751 issued to Fletcher et al., on Aug. 28, 2001; U.S. Pat. No. 6,506,394 issued to Yohiaoui et al., on Jan. 14, 2003; U.S. Pat. No. 6,440,437 issued to Krzysik et al., on Aug. 27, 2002; U.S. Pat. No. 6,630,175 issued to Shapiro et al., on Oct. 7, 2003; EP 228,868, to Farrar et al., published Jul. 15, 1987; WO 97/39733 A1, published on Oct. 30, 1997; U.S. Patent Application No. US20030190337A1: "Methods for regulating the condition of mammalian keratinous tissue via topical application of vitamin B6 compositions", published on Oct. 9, 2003; U.S. Patent Application No. US20030130636A1: "System for improving skin health of absorbent article wearers", published on Jul. 10, 2003; and U.S. Patent Application No. US20020177535A1: "Cleansing compositions with milk protein and aromatherapy", published on Nov. 28, 2002.

Mixtures of the above components may also be used.

Additionally, the benefit composition may be applied to the nonwoven sheet member in any suitable fashion, such as but not limited to, as a complete benefit composition or at different times in the form of the various components of the benefit composition. Alternatively, the various components of the benefit composition may be placed at different regions on the nonwoven sheet member, e.g. the various amphibious markings 342 may be different components, or mixtures thereof of the benefit composition.

Each of the components of the benefit compositions, when present, are each typically employed in benefit compositions at levels of from about 0.0001% to about 99.9%, preferably from about 0.001% to about 99%, and more preferably from about 0.01% to about 97%, by weight of the benefit composition.

In preparing the disposable child sized article of the present invention the benefit composition need to be releasably carried by the disposable child sized article, such as placed on and/or in the nonwoven sheet member. Techniques for combining the disposable child sized article or nonwoven sheet member with the personal care composition are well known in the art. Examples of common methods of combining the benefit composition with the disposable child sized article may involve coating, immersing, dipping, printing, and/or spraying, a nonwoven sheet member with the benefit composition. The benefit composition of is added to the disposable child sized article at level sufficient to provide the desired benefits of the present invention. A convenient method of combining the benefit composition of the present invention with the disposable child sized article is for the benefit composition to be applied to a nonwoven sheet member while the nonwoven sheet member is a continuous web. The application could be in many forms, including one or more of, but not limited to coating, immersing, dipping, spraying, printing, extruding and the like. Once the benefit composition is applied the nonwoven sheet member is cut to the desired length to form the disposable child sized article and then packaged for sale. Alternatively, the benefit composition may be added to a nonwoven sheet member when the nonwoven sheet member is part of a fully or partially formed disposable child sized article.

The benefit composition may be added to the disposable child sized article in any convenient fashion. For example, the benefit composition components could all be mixed together and then sprayed onto a nonwoven sheet member; each component could be deposited on a nonwoven sheet member separately; or half the components could be mixed together and then added to a nonwoven sheet member, with the remainder then being mixed together and then sprayed on to a nonwoven sheet member.

In one optional embodiment of the present invention, the benefit composition is applied to a nonwoven sheet member, in the form of a paste prior to the assembly of the disposable child sized article. This optional embodiment is more preferably a "hot melt" composition. Hot melt composition have high viscosity at or around room temperature, and then melt (become substantially liquid) at higher temperatures. Such systems are advantageous during processing of a disposable, substantially dry (or dry to the touch) child sized article since the composition can be applied (e.g., coated, sprayed, extruded) to the nonwoven sheet member at a low viscosity (e.g., a liquid) at higher than room temperature, and then as the composition cools down, it becomes a high viscosity paste or solid.

Once the benefit composition is applied to the disposable child sized article and/or nonwoven sheet member it may be further treated in any conventional manner, such as but not limited to, heating to remove excess water from the benefit composition.

Child Graphic

The child graphic may be any suitable visual image or images. The child graphic may include pictorial symbols and/or images, such as but not limited to, photographs, such as but not limited to: a photograph of a child using the disposable child sized article; drawings, such as a drawing of a child or an anthropomorphic image of an animal or object using the disposable child sized article; cartoons, such as but not limited to, well known cartoon characters, caricatures of famous people, well known brand logos or the like, or characters specifically created to be associated with the article of commerce; symbols, such as but not limited to arrows, indications or motion or movement, and the like; and combinations thereof.

Figure 12:
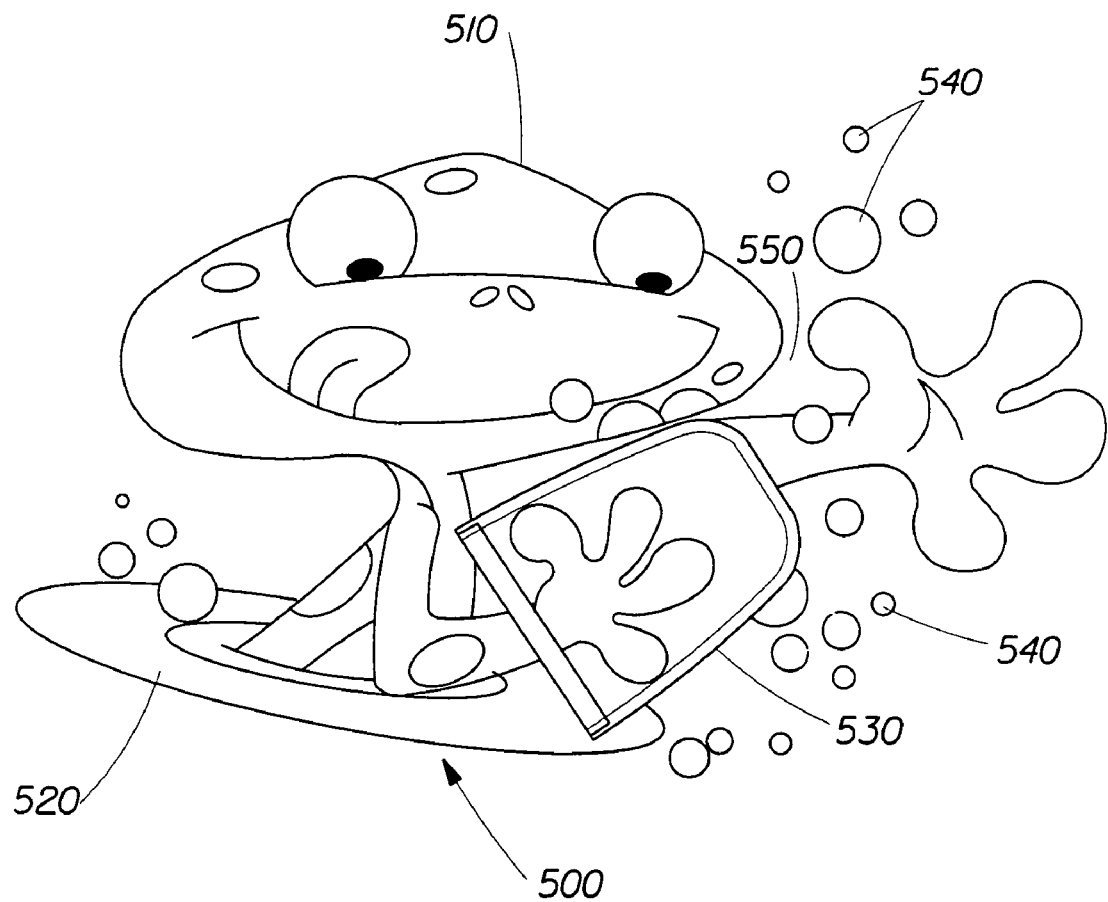
FIG. 12 illustrates one exemplary child graphic.

The child graphic may be arranged in any suitable fashion and may be in the form of one or more pictorial images. The arrangement may include the child graphic in, for example, a single image or picture, such as in a single image or a single cartoon. FIG. 12 illustrates a single image 500 which includes a child graphic. The child graphics present in image 500 include an anthropomorphic animal 510, in this case a frog, who is in a body of water 520, holding a disposable child sized article 530 in his hand. Optionally, the disposable child sized article illustrated in the child graphic or child graphics is similar in appearance, at least to a child, to any disposable child sized article in association with the child graphic or child graphics. The image further illustrates that frog 520, is cleaning himself thereby generating suds and bubbles 540 using the disposable child sized article 530 by contacting parts of his body 550 with the disposable child sized article 530.

Figure 13:
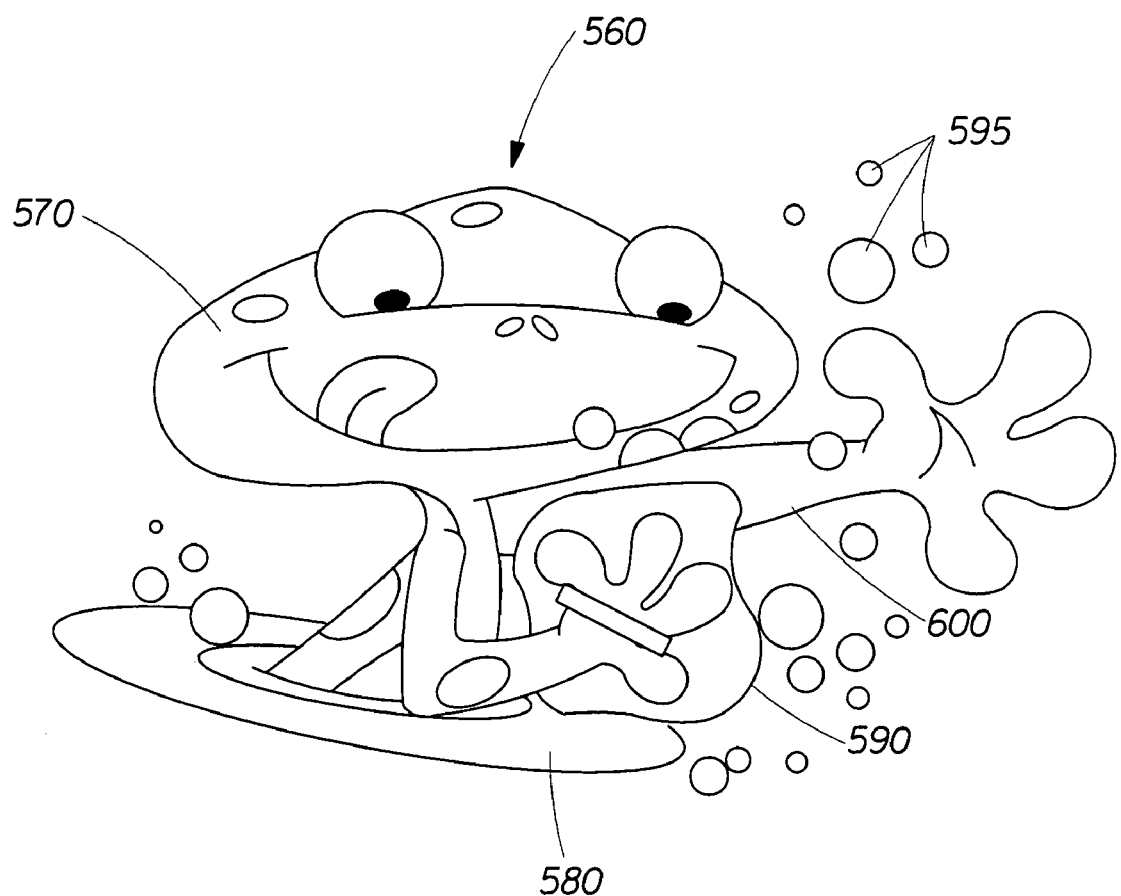
FIG. 13 illustrates another exemplary child graphic.

FIG. 13 similarly illustrates a single image 560 which includes a child graphic. The child graphics present in image 560 include an anthropomorphic animal 570, in this case a frog, who is in a body of water 580, holding a disposable child sized article 590, which is similar to the disposable child sized article illustrated in FIG. 2, in his hand. The image further illustrates that frog 570, is cleaning himself thereby generating suds and bubbles 595 using the disposable child sized article 590 by contacting parts of his body 600 with the disposable child sized article 590.

Figure 14:
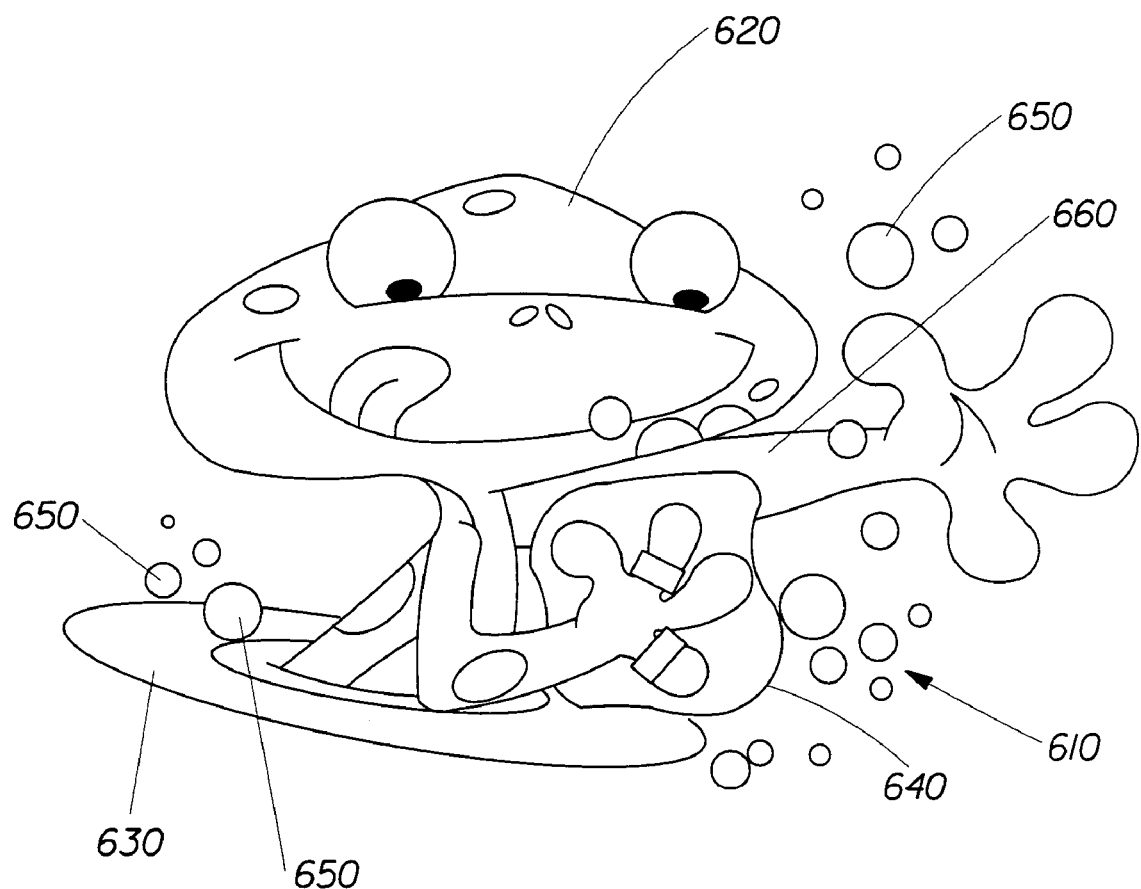
FIG. 14 illustrates another exemplary child graphic.

FIG. 14 similarly illustrates a single image 610 which includes a child graphic. The child graphics present in image 610 include an anthropomorphic animal 620, in this case a frog, who is in a body of water 630, holding a disposable child sized article 640, which is similar to the disposable child sized article illustrated in FIG. 6, in his hand. The image further illustrates that frog 620, is cleaning himself thereby generating suds and bubbles 650 using the disposable child sized article 640 by contacting parts of his body 660 with the disposable child sized article 640.

In an optional embodiment of the present invention, the child graphic is a sequential series of panels, wherein each of the panels contains, for example, a different cartoon, symbol, drawing, photograph and combinations thereof. Alternatively, each panel may contain one or more child graphic. These panels may be arranged in any suitable sequential fashion, such as but not limited to, vertically, horizontally, diagonally, circular, and the like and combinations thereof. Examples of this optional embodiment can be found in FIGS. 15, 16, and 17.

Figure 15:
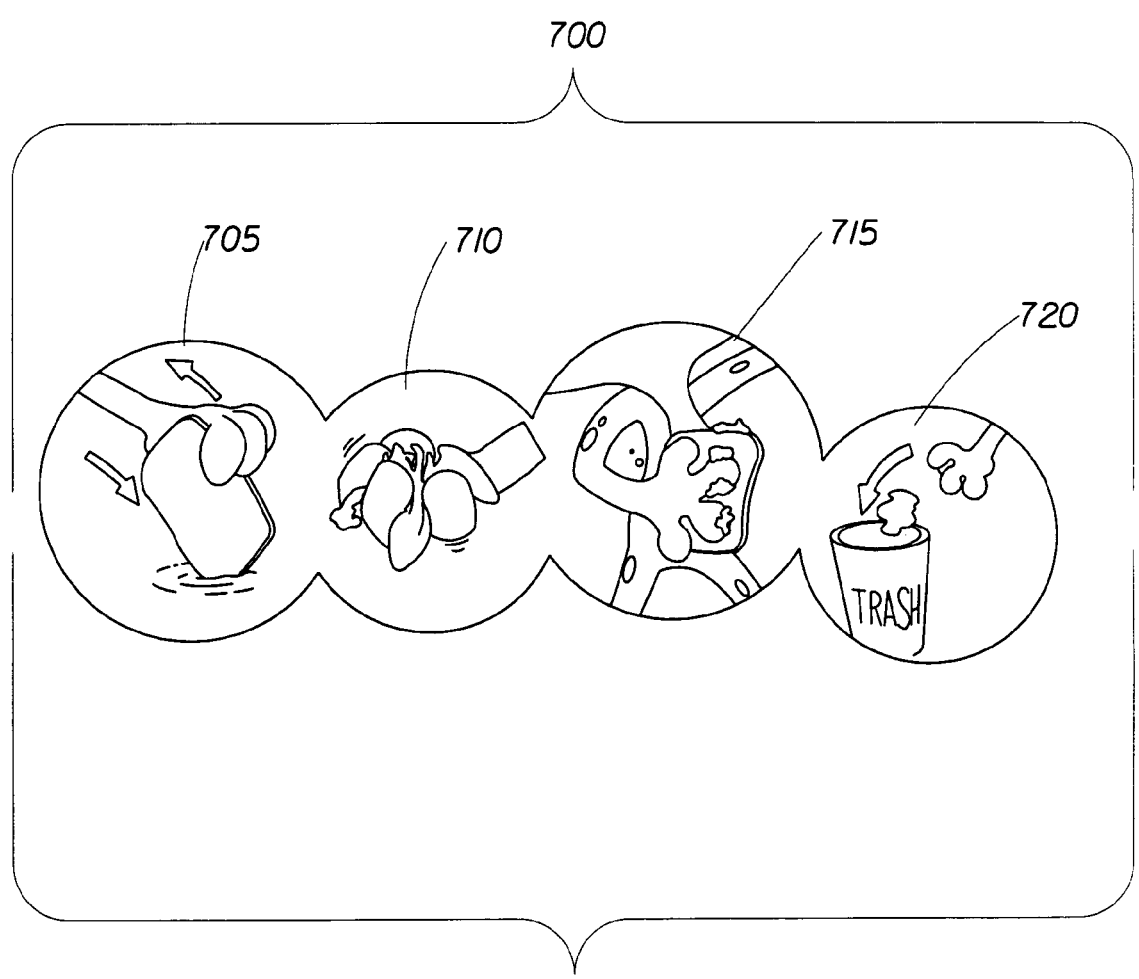
FIG. 15 illustrates another exemplary child graphic.

In FIG. 15, panels 700 are a child graphic comprising a sequential series of panels communicating, especially communicating to a child incapable of reading, how to use a disposable child sized article which is similar to the disposable child sized article illustrated in FIG. 6. Panel 705 visually communicates that the child needs to contact the disposable child sized article with water, such as, by immersion in a body of water such as a bath. Panel 710 also visually communicates through arrows how a child immerses the disposable child sized article. Panel 710 visually communicates that the benefit composition, which in this case may be a personal care composition, will generate lather. Furthermore, panel 710 visually communicates through the use of a hand and motion lines, that the child needs to squeeze or exert some compressive force on the disposable child sized article after contact it with water to generate foam. The frog character in panel 715 communicates to the child that in order to clean themselves they need to contact, such as by rubbing, scrubbing and the like, their body with the disposable child sized article. Panel 715 further communicates to the child that the disposable cleaning implement is suitable for use on the child's entire body. Panel 720 communicates the need for the child to properly dispose of the disposable child sized article after they have finished bathing.

Figure 16:
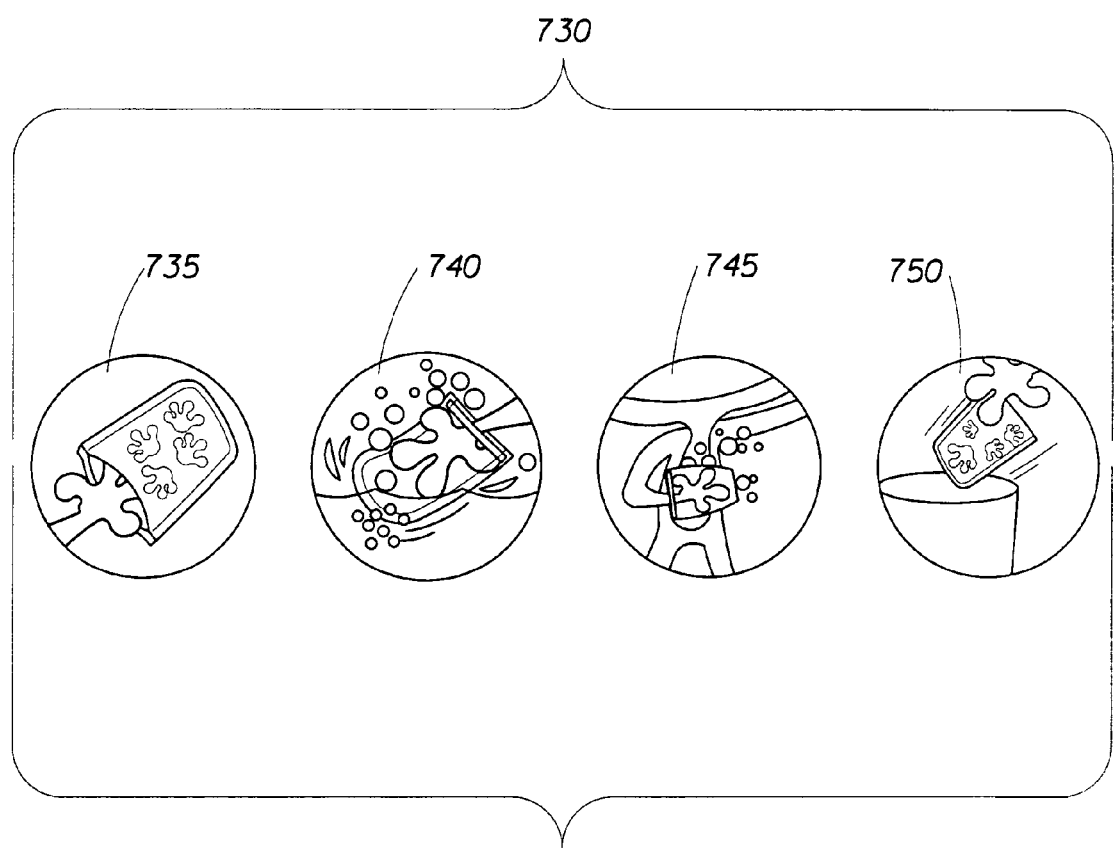
FIG. 16 illustrates another exemplary child graphic.

In FIG. 16, panels 730 are a child graphic comprising a sequential series of panels communicating to a child incapable of reading how to use a disposable child sized article which is similar to the disposable child sized article illustrated in FIG. 3. Panel 735 communicates where the child places its hand and the orientation of the disposable child sized article relative to the child. Panel 740 communicates that the child needs to contact the disposable child sized article with water, such as by immersion in a body of water such as a bath. Panel 740 also communicates to the child that the benefit composition is only present on one side of the disposable child sized article. Additionally, panel 740 reinforces the prior communication in panel 735 on the correct orientation of the disposable child sized article relative to the child. Panel 745, that is the frog character, additionally communicates to the child that in order to clean themselves they need to contact, such as by rubbing, scrubbing and the like, their body with the side of the disposable child sized article which will generate lather. Additionally, panel 745 further reinforces the prior communication in panels 735 and 740 on the correct orientation of the disposable child sized article relative to the child. Panel 750 communicates the need for the child to properly dispose of the disposable child sized article after they have finished bathing.

Figure 17:
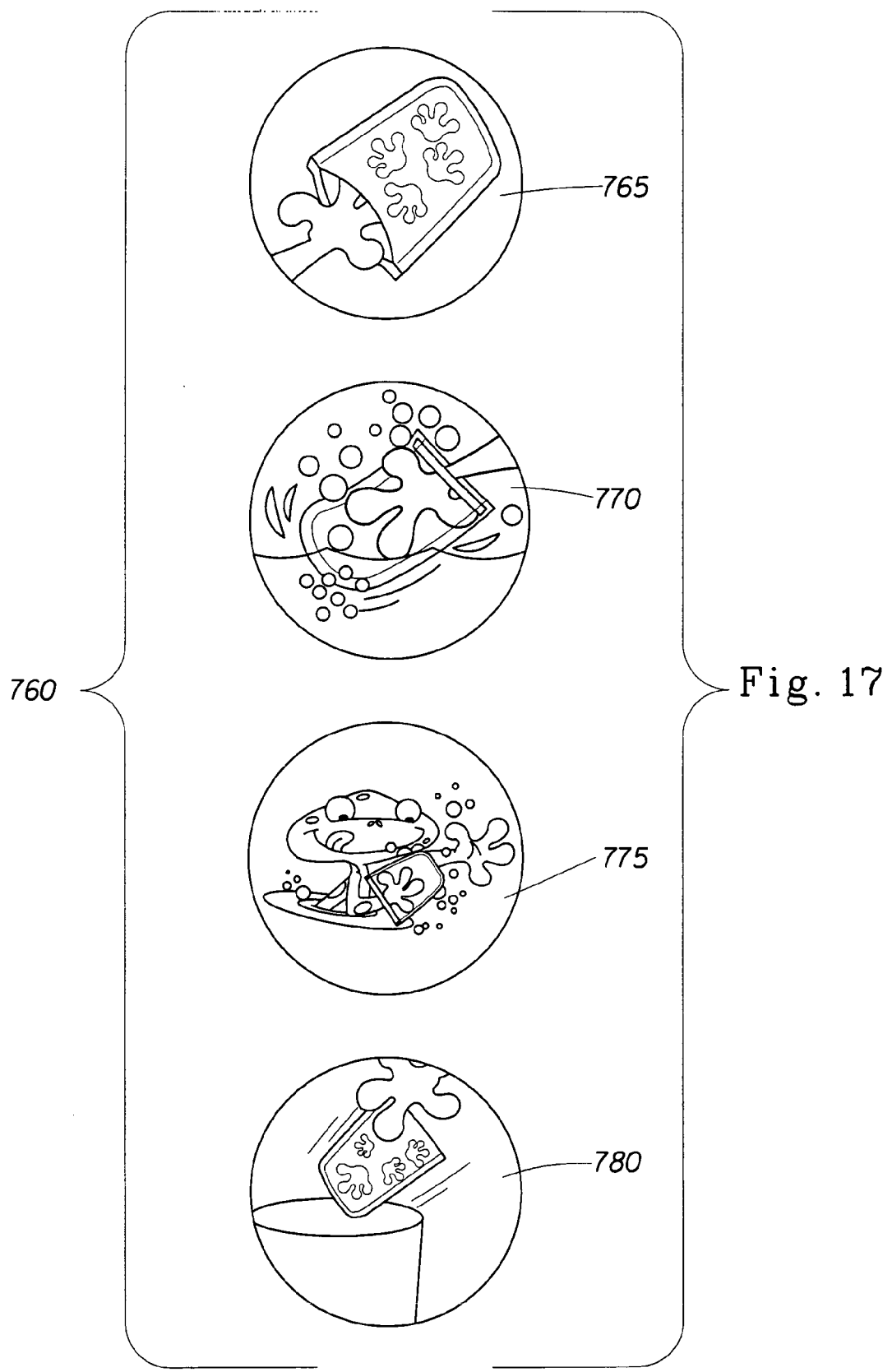
FIG. 17 illustrates another exemplary child graphic.

In FIG. 17, panels 760 are a sequential series of panels each comprising a different child graphic that are communicating, especially communicating to a child incapable of reading, how to use a disposable child sized article which is similar to the disposable child sized article illustrated in FIG. 3. Panel 765 communicates where the child places its hand to wear the disposable child sized article and the correct orientation of the disposable child sized article relative to the child. Panel 770 communicates not only that the child needs to contact the disposable child sized article with water, such as by immersion in a body of water such as a bath, but that the benefit composition will generate lather when combined with water. Panel 770 also communicates to the child that the benefit composition is only present on one side of the disposable child sized article. Additionally, panel 770 reinforces the prior communication in panel 765 on the correct orientation of the disposable child sized article relative to the child. Panel 775 reinforces the information communicated in previous panels 765 and 770 by again communicating that the benefit composition will generate lather and is only present on one side of the disposable child sized article. Panel 775 additionally communicates to the child that in order to clean themselves they need to contact, such as by rubbing, scrubbing and the like, their body with the side of the disposable child sized article which will generate lather. The frog character in panel 775 communicates to the child that the disposable child sized article is suitable for use while they are in a bath or similar body of water. Panel 780 communicates the need for the child to properly dispose of the disposable child sized article after they have finished bathing.

Figure 18:
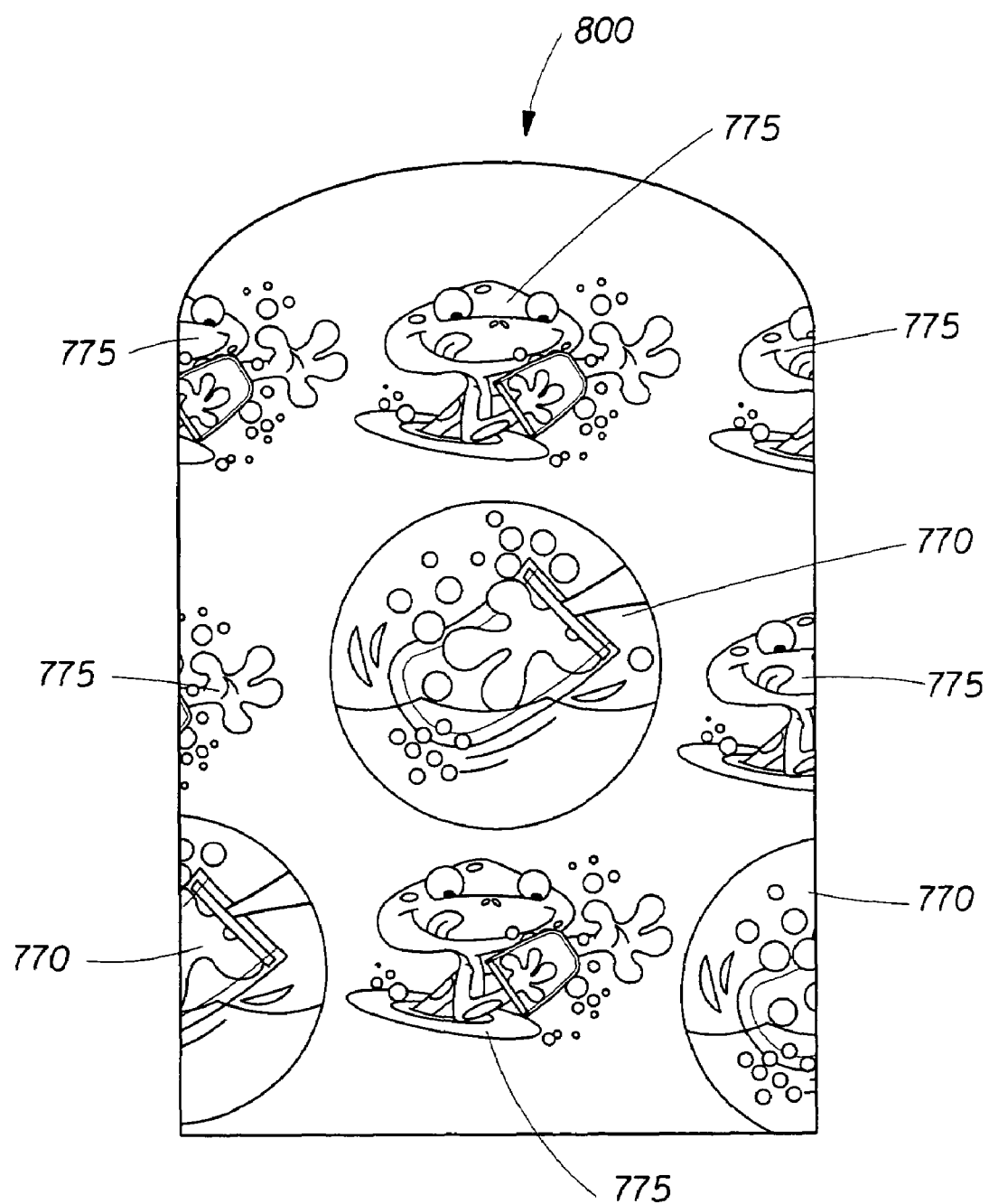
FIG. 18 illustrates one embodiment of a disposable child sized article having a child graphic thereon.

FIG. 18 shows a disposable child sized article 800 containing a repeating pattern of two of the child graphics of FIG. 17, namely a repeating pattern of panels 770 and 775. Disposable child sized article 800 may be used in combination with a container which has, for example, printed thereon the entire set, or only panels 765 and 780, of FIG. 17. These panels on the disposable child sized article 800 would provide additional reinforcement to the child as to the correct use of the disposable child sized article 800.

Figure 19:
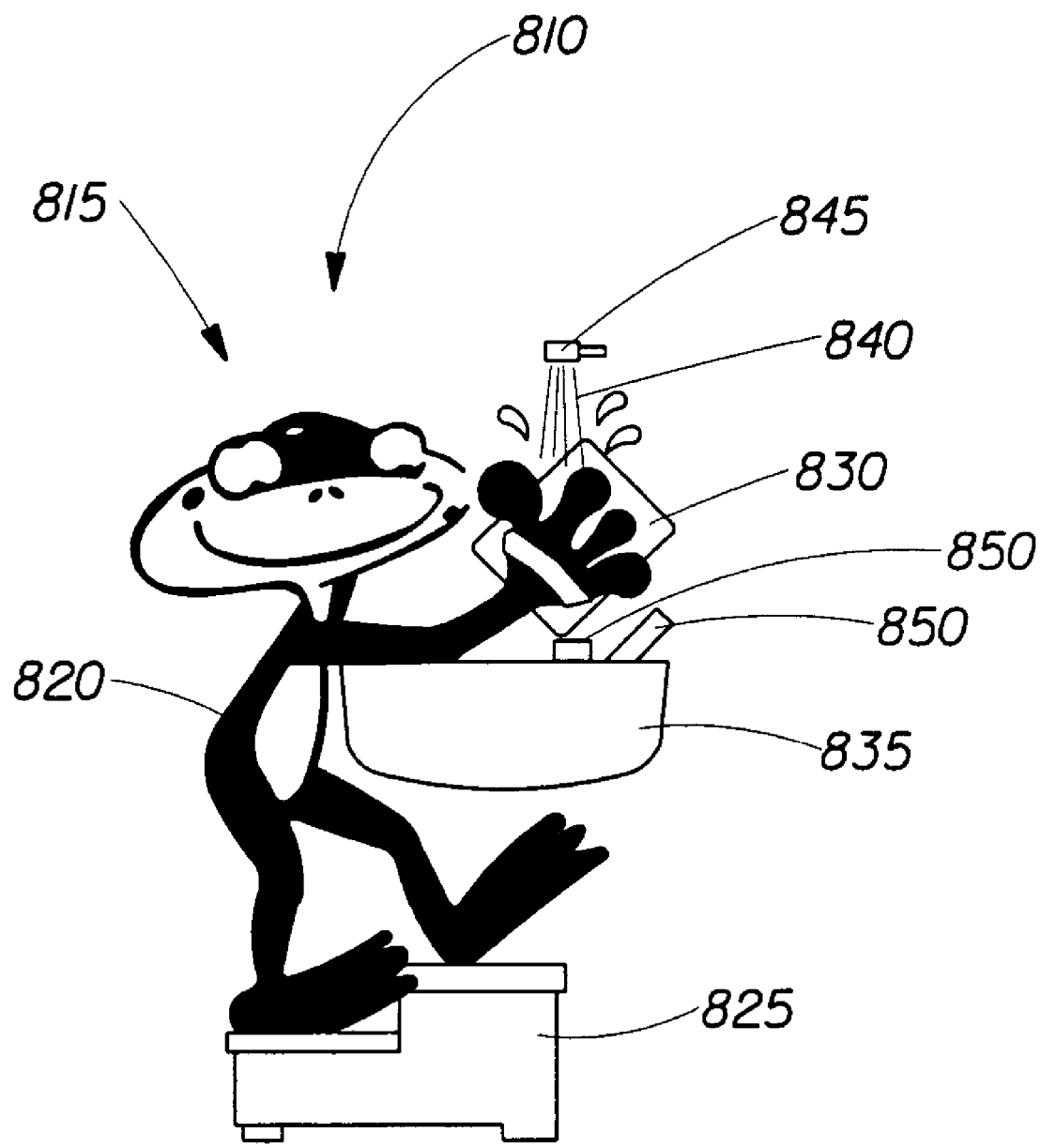
FIG. 19 illustrates another exemplary child graphic.

FIG. 19 similarly illustrates a single image 810 which includes a child graphic 815. The child graphic 815 present in image 810 includes a character graphic, specifically an anthropomorphic animal 820, in this case a frog, who is standing on a step stool 825 in front of a sink 835 into which water 840 is being added to via tap or faucet 845. The sink 835 also holds dirty or soiled tableware 850, such as dishes, cups, flatware and the like. The frog 820 is holding a disposable child sized article 830, which is similar to the disposable child sized article illustrated in FIG. 2, in his hand. The image 810 further illustrates that frog 820, is using the disposable child sized article 830 to clean the tableware 850 himself.

Figure 35:
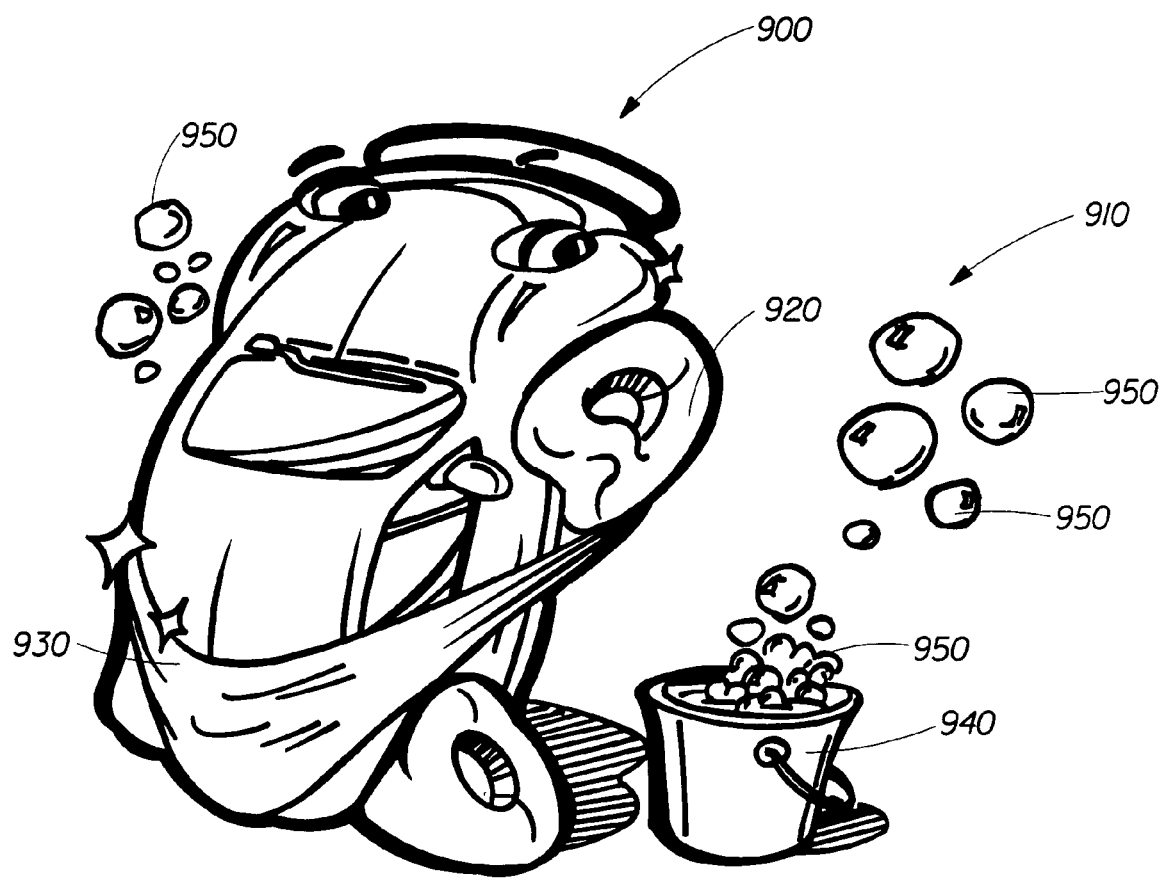
FIG. 35 illustrates another exemplary child graphic.

FIG. 35 illustrates an image 900 which includes a child graphic 910. The child graphic 910 present in image 900 includes a character graphic, specifically an anthropomorphic object 920, in this case an automobile, who is standing and drying itself with a towel 930. The image 900 further includes a bucket 940 which is full of a liquid which is generating bubbles 950.

FIGS. 20 to 35 illustrate additional exemplary child graphics, depicting a character, in these figures frogs, monkeys, turtle or automobile in a range of various activities that a child may typically be engaged in or would readily be able to imaging themselves in that action or activity, either in place of the character or doing the activity along with the character.

Figure 20:
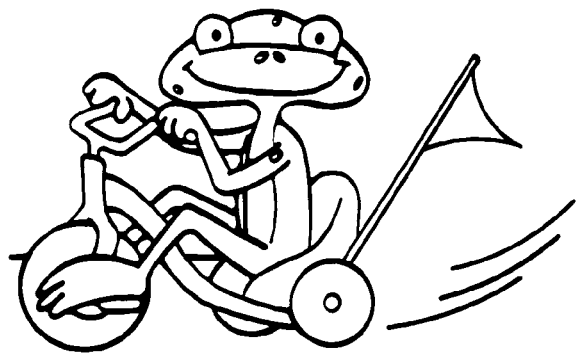
FIG. 20 illustrates another exemplary child graphic.
Figure 21:
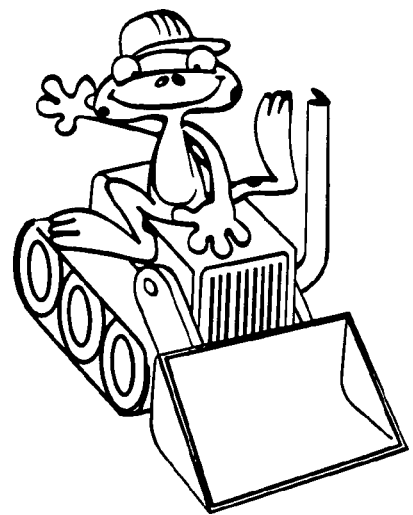
FIG. 21 illustrates another exemplary child graphic.
Figure 22:
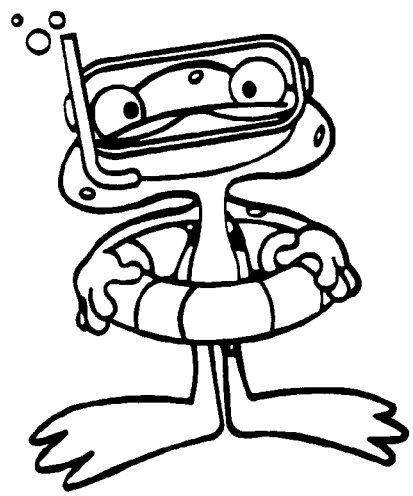
FIG. 22 illustrates another exemplary child graphic.
Figure 23:
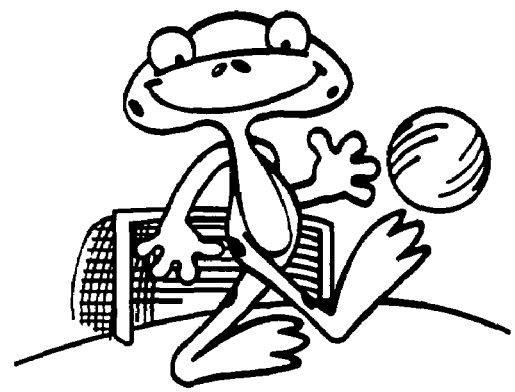
FIG. 23 illustrates another exemplary child graphic.
Figure 24:
FIG. 24 illustrates another exemplary child graphic.
Figure 25:
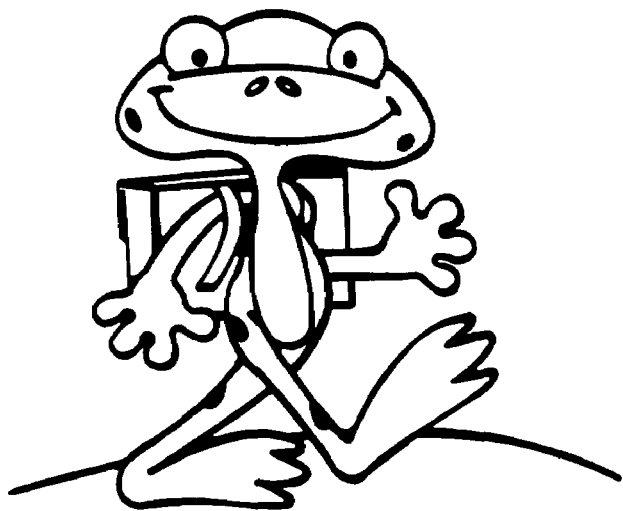
FIG. 25 illustrates another exemplary child graphic.
Figure 26:
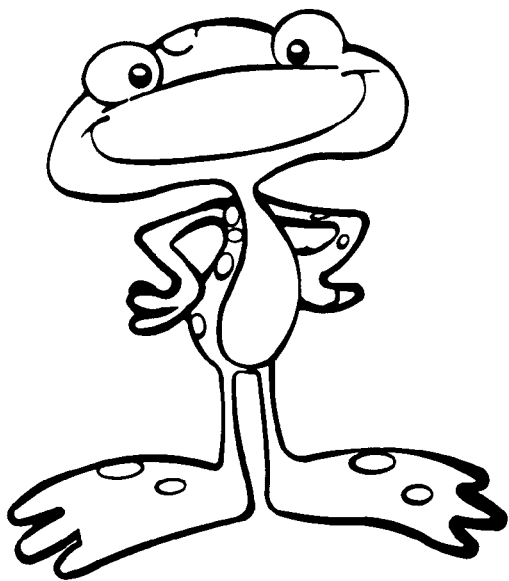
FIG. 26 illustrates another exemplary child graphic.
Figure 27:
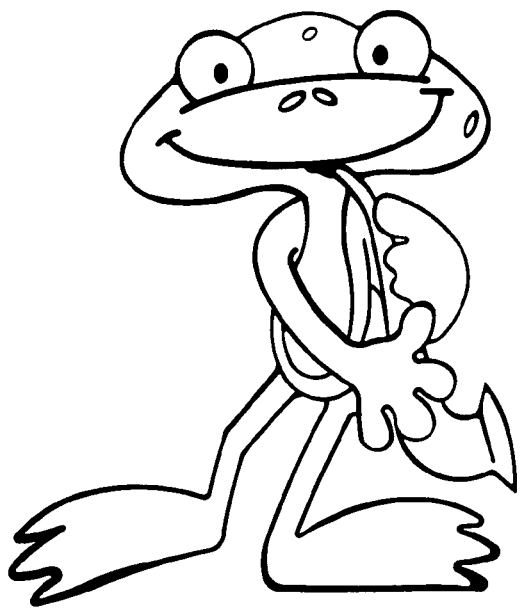
FIG. 27 illustrates another exemplary child graphic.
Figure 28:
FIG. 28 illustrates another exemplary child graphic.
Figure 29:
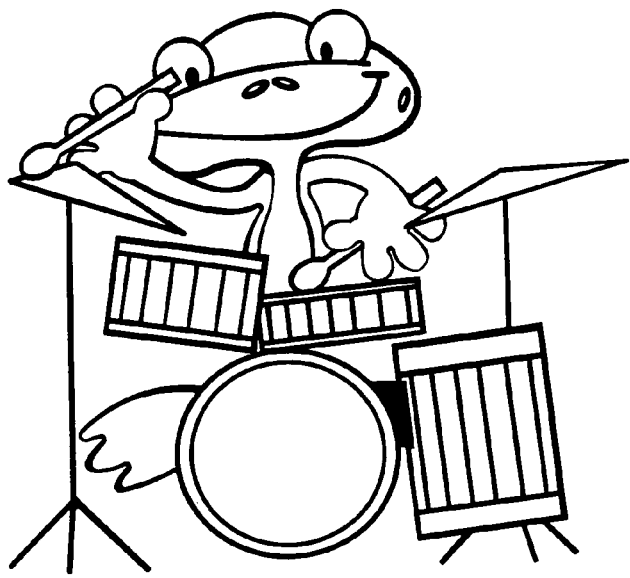
FIG. 29 illustrates another exemplary child graphic.
Figure 30:
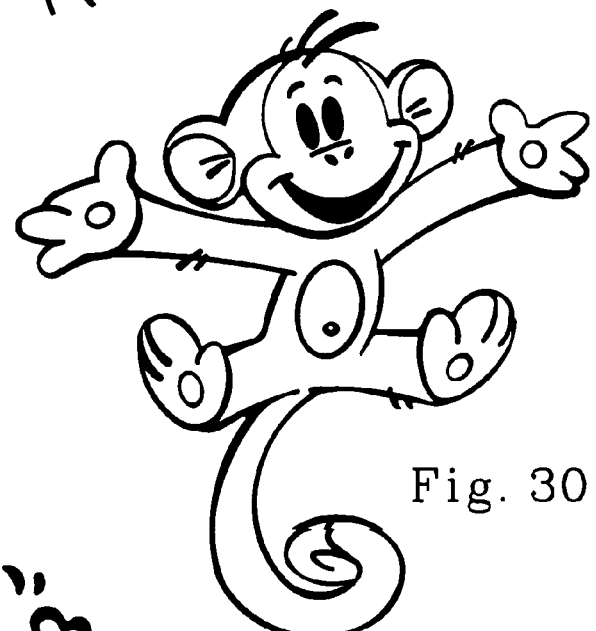
FIG. 30 illustrates another exemplary child graphic.
Figure 31:
FIG. 31 illustrates another exemplary child graphic.
Figure 32:
FIG. 32 illustrates another exemplary child graphic.
Figure 33:
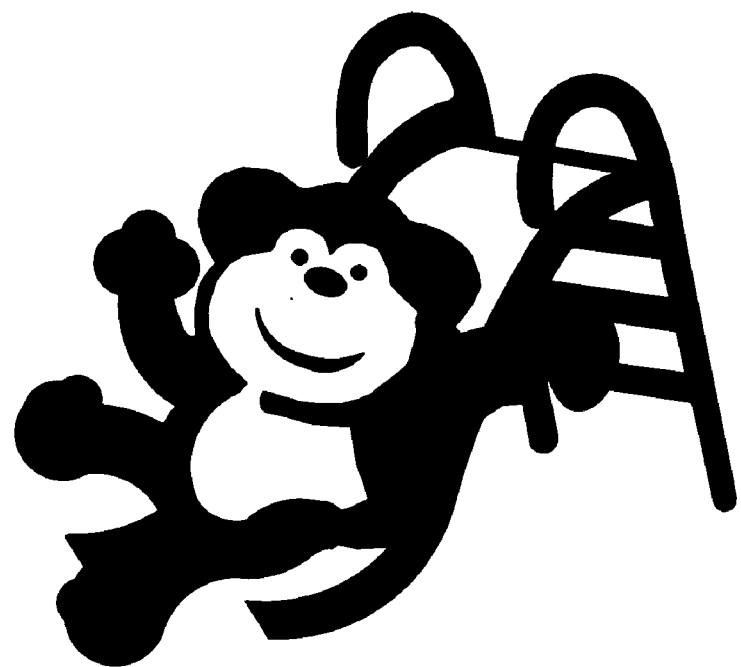
FIG. 33 illustrates another exemplary child graphic.

The child graphic or child graphics may also include a story line in which a character, such as the frogs, monkeys, turtle and automobile of FIGS. 12 to 35, are illustrated performing an activity which may lead to the character needing to perform an activity which may involve the use of the disposable child sized article. Illustrative, but non limiting examples of such activities include, running, riding (for example, riding a tricycle as illustrated in FIG. 20 or a bulldozer as illustrated in FIG. 21), playing in the mud, playing with a ball (FIG. 23), playing hide and seek, or other similar activities which a child does and can relate to. In this way, the child graphic or child graphics may permit the caregiver to interact with the child regarding the story line created by the child graphic or child graphics and may provide an opportunity for the caregiver to teach the child important life lessons, such as bathing and cleaning, due to the interactive nature of the child graphic.

In one alternative embodiment of the present invention, when the disposable child sized article comprises two or more child graphics, and/or the disposable child sized article is present in a container which has one or more child graphics, these different child graphics may be have a common storyline.

In one alternative embodiment of the present invention when the disposable child sized article comprises two or more child graphics, and/or the disposable child sized article is present in a container which has one or more child graphics, these different child graphics may be have a related in subject matter.

Figure 34:
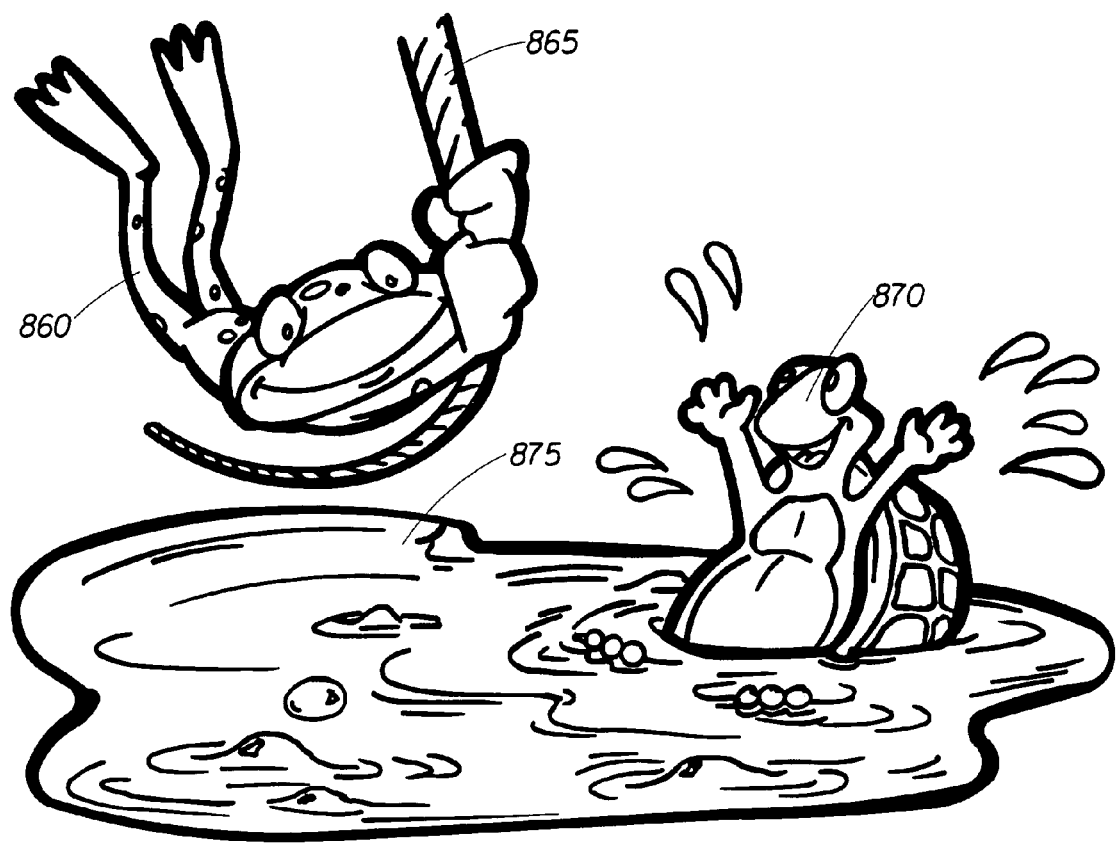
FIG. 34 illustrates another exemplary child graphic.

FIG. 34 illustrates a pair of child graphics, in this case two character graphics, a frog 860 and a turtle 870 which have a common story line and are related in subject matter. The frog 860 is swinging on a rope 865 over a pool or pond 875 in which the turtle 870 is frolicking and splashing.

In one alternative embodiment of the present invention when the disposable child sized article comprises two or more child graphics, and/or the disposable child sized article is present in a container which has one or more child graphics, these different child graphics may be have a unrelated in subject matter.

The child graphic may optionally include a character graphic that can increase the child's interest in using the disposable child sized article and can increase the opportunities for the caregiver to interact positively with the child. The term "character graphic" is used herein to refer to a child graphic containing an anthropomorphous image, and in particular an image having or suggesting human form or appearance which ascribes human motivations, characteristics or behavior to inanimate objects, animals, natural phenomena, toys, cartoon characters, or the like. Ideally the character graphic would be suitable for children's swimwear, toys, clothing, diapers or the like and could be utilized to motivate children to use the disposable child sized article. To that end, the character graphics can be associated with popular characters in the media, advertising or well known in a particular culture. Ideally they are characters that the child or caregiver care about and want to identify with. Ideally the child can imagine himself or herself taking the place of the character or emulate the character's behavior/attitude.

The role of the character graphic in the child graphic can be to encourage a child and to motivate them to behaviors, such as but not limited to, cleaning themselves, cleaning their room, and the like. The character graphic may provide a source of entertainment and reassurance for the child and a buddy, or friend, who reduces stress and can be related to in a non-competitive fashion during the training period. The character may also provide positive reinforcement and encouragement to the child while the child is learning new skills and behaviors in a non-competitive or threatening manner.

Suitable character graphics can include animals, people, inanimate objects, natural phenomena, cartoon characters or the like, that can or can not be provided with human features such as arms, legs, facial features or the like. It may be desirable for the character graphic to be familiar to the child, such as an identifiable cartoon character. The character graphics should at least be a type that the child can relate to, examples of which could include animals, toys, licensed characters, or the like. Character graphics can be made more personable and friendly to the child by including human-like features, human-like expressions, apparel, abilities, or the like. In one optional embodiment it is desirable for a character to have a distinguishing feature or features, which in a pictograph can help in training, such as a frog's webbed hand. By way of illustration, an animal character graphic can be shown smiling, wearing clothing, playing sports, fishing, driving, playing with toys, or the like. In particular embodiments, the character graphic can desirably be created to project an appearance that could be described as friendly, positive, non-intimidating, silly, independent, inspirational, active, expressive, dauntless and/or persevering. For example, the frog 510 of FIG. 12 is one example of such a character graphic and is intended to inspire the child to learn how to bathe and clean themselves. The frog's expression clearly shows that while he is concentrating on cleaning himself and becoming independent, he is still smiling and having fun. Additionally, it is preferred that the characters expressions are exaggerated so as to not be too subtle for a child to understand.

Furthermore the combination of story line and character graphics are believed to make children more interested in the use of the disposable child sized article, such as but not limited to an article for use in a bathing or cleaning process, and therefore lead to enhanced results. While not wishing to be limited by theory it is believed that the child graphic and the other elements of the disposable child sized article work together to provide to a child, and especially those who are incapable of reading, the appropriate tools, directions in the use of those tools and positive reinforcement which enables the child to learn how to, for example clean themselves, wash their hair, clean their room, and the like.

The character graphic, or parts thereof may retain essentially the same appearance and/or shape while the child is using the disposable child sized article. Alternatively, the character graphic, or parts thereof may, change appearance, shape, appear and/or disappear while the child is using the disposable child sized article. That is a use indicator may be optionally a part of a child graphic, or a child graphic when more than one child graphic is present. This change may occur in any suitable manner or fashion, such as but not limited to exposure to a specific environment (e.g., water, air, other suitable chemicals, a pH or pH range), time, abrasion or similar physical force or contact, and the like and combinations thereof. One example of this may be a character who is gesturing hello, welcome or the like, is changed after the child has immersed the article in water and uses the article, to gesture goodbye.

In one optional embodiment the child graphic may optionally include a character graphic which is associated with a line of children's consumer products, such as but not limited to personal cleansing products and the like. The character may be one of a family, group, team, or the like, each member of which is designed to be associated with, for example, a consumer product, a cleaning event such as washing hair, an age group, stage of infant development and the like. Alternatively, all of the characters of a family, group, team, or the like, may be designed to be associated with the entire range of consumer products.

The association by the child of the character with the consumer product, cleaning event, etc., encourages and provides a way for the child to visualize through their imagination the character using the disposable child sized article in the way intended. Furthermore, since this teaching is through the use of the child's imagination, there are none of the negative connotations associated with conventional parental instruction on how to use a consumer product, such as the disposable child sized article. Instead of the child being subjected to parental nagging to do something the child really doesn't want to do, the child will actively use the disposable child sized article as part of active learning play to interact with their new buddy, or friend, and imitate behavior. The interaction between the child and the character is only limited by the bounds of the child's imagination. The role of the caregiver or parent in then becomes one of actively encouraging imaginative play by the child with the character to use the disposable child sized article correctly, instead of a being perceived by the child as a parent who stops play. Play is actively encouraged and new skills become part of play; "uninterrupted play". Since the use of the disposable child sized article is essentially play, the child is eager to use the disposable child sized article and learn the skill.

A family or group of character graphics can be used to progress a child through a system of consumer products, especially systems including the disposable child sized article and the like. In this embodiment each character of the family or group, would be tailored to appeal to different groups of children. These groups may be based on age, development stages, regions, etc. Alternatively, a single character may be tailored for one particular group consumer products of line of consumer products which are different for children at different ages, development stages, etc. In this case the character may, for example be, of a different age depending on the consumer product and which group of children the product is intended to be used by.

Child graphics, such as, but not limited to, character graphics act to enable and encourage the desired behavior, such as the correct use of the disposable child sized article, by providing stimuli. For example, in the case of a child graphic containing a character the stimuli may be entertainment and a friend.

Container

In one optional embodiment of the present invention, the disposable child sized article may be present in a container. The container may be any suitable container which is capable of removably holding at least one disposable child sized article. The container may be rigid or it may be semi-rigid. Typically, any container will have a portion for storage of the disposable child sized article. The size of the storage portion will depend upon the many factors, such as but not limited to, the size of the disposable child sized article(s), the number of disposable child sized articles initially present in the container, ease of use by a child, etc. This storage portion may be accessed in any suitable fashion through an opening, or orifice of a size which is suitable for the size of the disposable child sized article.

Containers useful include, but are not limited, PET tubs, flow wrap pouches, precut sachets for individually packed disposable child sized article's, and other packaging known in the art as suitable for nonwoven articles releasably carrying a composition, such as but not limited to reach in or so called pop-up containers.

Furthermore, when present the container may be in the shape of a character, such as, but not limited to, a character present in the child graphics present one or more of the disposable child sized article.

Additional information on containers, as well as additional option components for containers, including but not limited to: container bodies; lids; containers features, such as but not limited to, attachments of lids, hinges, zippers, securing means; and the like, can be found in U.S. Pat. Nos. Des 451,279 issued on Dec. 4, 2001, to Chin; Des 437,686 issued on Feb. 20, 2001, to Balzar; Des 443,508 issued on Jun. 12, 2001, to Braaten; Des 443,451 issued on Jun. 12, 2001, to Buck; Des 421,901 issued on Mar. 28, 2000, to Hill; Des 421,902 issued on Mar. 28, 2000, to Hill; Des 416,794 issued on Nov. 23, 1999, to Cormack; Des 414,637 issued on Oct. 5, 1999, to Amundson; Des 445,329 issued on Jul. 24, 2001, to Zethoff; U.S. Pat. No. 3,982,659 issued on Sep. 26, 1976, to Ross; U.S. Pat. No. 3,967,756 issued on Jul. 6, 1976, to Barish; U.S. Pat. No. 3,986,479, issued on Oct. 19, 1976, to Boedecker; U.S. Pat. No. 3,994,417 issued on Nov. 30, 1976, to Boedecker; U.S. Pat. No. 6,269,970 issued on Aug. 7, 2001, to Huang; U.S. Pat. No. 5,785,179 issued on Jul. 28, 1998, to Buczwinski; U.S. Pat. No. 5,366,104 issued on Nov. 22, 1994, to Armstrong; U.S. Pat. No. 5,322,178 issued on Jun. 21, 1994, to Foos; U.S. Pat. No. 5,050,737 issued on Sep. 24, 1991, to Josyln; U.S. Pat. No. 4,971,220 issued on Nov. 20, 1990, to Kaufman; U.S. Pat. No. 6,296,144 issued on Oct. 2, 2001, to Tanaka; U.S. Pat. No. 6,315,114 issued on Nov. 13, 2001, to Keck; U.S. Pat. No. 4,840,270 issued on Jun. 20, 1989, to Caputo; U.S. Pat. No. 4,471,881 issued on Sep. 18, 1984, to Foster; U.S. Pat. No. 5,647,506 issued on Jul. 15, 1997, to Julius; U.S. Pat. No. 6,401,968 issued on Jun. 11, 2002, to Huang; U.S. Pat. No. 6,269,969 issued on Aug. 7, 2001, to Huang; U.S. Pat. No. 6,412,634 issued on Jul. 2, 2002, to Telesca; U.S. Pat. No. 5,791,465 issued on Aug. 11, 1998, to Niki; U.S. Pat. No. 6,092,690 issued on Jul. 25, 2000, to Bitowft; and U.S. Pat. No. 6,092,690 issued on Jul. 25, 2000, to Bitowft; U.S. Patent Application Publication No. 2002/0064323 published on May 30, 2002, inventor Chin; and WO 00/27268 published on May 18, 2000, and assigned to The Procter & Gamble Co.; WO 02/14172 published on Feb. 21, 2002, and assigned to The Procter & Gamble Co.; and WO 99/55213 published on Nov. 4, 1999, and assigned to The Procter & Gamble Co.

EXAMPLES

Example 1

A disposable child sized article comprising a 105 mm×140 mm rectangle comprising 60 gsm polyester nonwoven high loft batting material, Proef 1297 available from Libeltex of Meulebeke Belgium. The high loft batting material is releasably carrying 50 gsm of a benefit composition, which is a personal care composition, specifically BC20, available from Rhodia of France. Disposed on one side of the nonwoven high loft batting material is the child graphic illustrated in FIG. 12. Disposed on the other side of the nonwoven high loft batting material is retaining aid which is illustrated in FIG. 3.

Example 2

A disposable child sized article according to Example 1, except that the retaining aid and the child graphic are those illustrated in FIGS. 2 and 13 respectively.

Example 3

A disposable child sized article according to Example 1, except that the retaining aid and the child graphic are those illustrated in FIGS. 6 and 14 respectively.

Example 4

A disposable child sized article according to Example 1, except that the child graphic is that illustrated in FIG. 16.

Example 5

A disposable child sized article according to Example 1, except that the nonwoven sheet member is a two-layer laminate. The first layer of the laminate is a 40 gsm PET spunlace. While the second layer of the laminate is a 60 gsm polyester nonwoven high loft batting material, Proef 1297 available from Libeltex of Meulebeke Belgium. The high loft batting material is releasably carrying the 30 gsm of benefit composition, which is a personal care composition, specifically BC20, available from Rhodia of France.

Example 6

A disposable child sized article according to Example 5, except that the child graphic is that illustrated in FIG. 18.

Example 7

A disposable child sized article according to Example 5, except that personal care composition comprises 15 gsm of a composition as follows:

| Component | % wt. |
|---|---|
| Sodium Laureth-3 Sulfate | 63.5 |
| Cocamidopropyl Betaine | 23.5 |
| PEG-200 Glyceryl Tallowate | 10.0 |
| Polyquaternium-10 | 1.0 |
| Preservative System | 0.5 |
| Whitener | 0.5 |
| Perfume | 0.5 |
| Water | (Quantity sufficient to 100%) |

Example 8

A disposable child sized article wherein the nonwoven sheet member is a two-layer laminate. The first layer of the laminate is a 40 gsm PET spunlace. While the second layer of the laminate is a 60 gsm polyester nonwoven high loft batting material, Proef 1297 available from Libeltex of Meulebeke Belgium. Disposed on one side of the nonwoven high loft batting material is the child graphic illustrated in FIG. 23. Disposed on the other side of the nonwoven high loft batting material is retaining aid which is illustrated in FIG. 3. The high loft batting material is also releasably carrying 10 gsm of the benefit composition, which is a hard surface cleaning composition, specifically one of A, B or C.

| | Weight % | | |
|---|---|---|---|
| Ingredients | A | B | C |
| Sodium paraffin sulfonate | 1.0 | 3 | 3 |
| Alcohol ethoxylate 7EO | 4 | — | — |
| Alcohol ethoxylate 30EO | — | 3 | 2 |
| C12-14 EO21 alcohol ethoxylate | 1.0 | — | — |
| C12MBAE3* | 5.0 | 1 | 2 |
| Sodium Citrate | 3 | 3 | 3 |
| Butylcarbitol$^R$ | 4 | 4 | 4 |
| Triethanolamine | 1 | 1 | 1 |
| water & minors | Quantity sufficient up to 100% (qs to 100%) | | |

*MBAE: mid-chain branched alkyl polyoxyalkylene surfactant having an average of three ethylene oxide groups.

Example 9

A disposable child sized article according to Example 8, except that the hard surface cleaning composition is a glass cleaning composition selected from one of D, E or F:

| Ingredient (% by weight) | D | E | F |
|---|---|---|---|
| Ethanol | 2.8 | 2.8 | 2.8 |
| Ethylene Glycol Monobutyl Ether | 2.8 | 2.8 | 2.8 |
| *C9MBAS | 0.3 | 0.3 | — |
| Sodium Alkyl ($C_8$, $C_{12}$, and $C_{14}$) Sulfate | 0.2 | — | 0.2 |
| Versaflex 7000 | — | — | 0.1 |
| Versaflex 2004 | — | 0.1 | — |
| Polymer[1] | 0.1 | — | — |
| Perfume, NaOH (to adjust pH to 9.5), and water to balance % | qs to 100% | | |

*MBAS: mid-chain branched alkyl sulfonate surfactant.
Versaflex 2004 and 7000 are sodium sulfonated polystyrenes from National Starch and Chemical Company.
[1]Vinyl pyrrolidone/acrylic acid copolymer (MW about 250,000)

Example 10

A disposable child sized article wherein the nonwoven sheet member is a 60 gsm polyester nonwoven high loft batting material, Proef 1297 available from Libeltex of Meulebeke Belgium. Disposed on one side of the nonwoven high loft batting material is the child graphic illustrated in FIG. 19. Disposed on the other side of the nonwoven high loft batting material is retaining aid which is illustrated in FIG. 2. The high loft batting material is also releasably carrying 25 gsm of the benefit composition, which is a LDL (Light duty detergent) composition, specifically one of G, H, or J.

| | weight % | | |
|---|---|---|---|
| Ingredients | G | H | J |
| $C_{12}$-$C_{15}$ Alkyl sulphate | — | 28.0 | 25.0 |
| $C_{12}$-$C_{13}$ Alkyl ($E_{0.6-3}$) sulfate | 30 | — | — |
| $C_{12}$ Amine oxide | 5.0 | 3.0 | 7.0 |
| $C_{12}$-$C_{14}$ Betaine | 3.0 | — | 1.0 |
| $C_{12}$-$C_{14}$ Polyhydroxy fatty acid amide | — | 1.5 | — |
| $C_{10}$ Alcohol Ethoxylate $E_9$[1] | 2.0 | — | 4.0 |
| Diamine[2] | 1.0 | — | 7.0 |
| $Mg^{2+}$ (as $MgCl_2$) | 0.25 | — | — |
| Citrate as K(citrate) | 0.25 | — | — |
| Minors and water[3] | qs to 100% | qs to 100% | qs to 100% |
| pH of a 10% aqueous solution adjusted to | 9 | 10 | 10 |

[1]$E_9$ Ethoxylated Alcohols as sold by the Shell Oil Co.
[2]1,3-diaminopentane sold as Dytek EP.
[3]Includes perfumes, dyes, ethanol, etc.

Example 11

A disposable child sized article according to Example 10, except that the LDL is selected from one of L, M or N.

| | weight % | | |
|---|---|---|---|
| Ingredients | L | M | N |
| $C_{12}$-$C_{13}$ Alkyl ($E_{0.6-3}$) sulfate | — | 15.0 | 10.0 |
| Paraffin sulfonate | 20.0 | — | — |
| Na $C_{12}$-$C_{13}$ linear alkylbenzene sulfonate | 5.0 | 15.0 | 12.0 |
| $C_{12}$-$C_{14}$ Betaine | 3.0 | 1.0 | — |
| $C_{12}$-$C_{14}$ Polyhydroxy fatty acid amide | 3.0 | — | 1.0 |
| $C_{10}$ Alcohol Ethoxylate $E_9$[1] | — | — | 20.0 |
| Diamine[2] | 1.0 | — | 7.0 |
| DTPA[3] | — | 0.2 | — |
| $Mg^{2+}$ (as $MgCl_2$) | 1.0 | — | — |
| $Ca^{2+}$ (as Ca(citrate)$_2$) | — | 0.5 | — |
| Protease[4] | 0.01 | — | 0.05 |
| Amylase[5] | — | 0.05 | 0.05 |
| Hydrotrope[6] | 2.0 | 1.5 | 3.0 |
| Minors and water[7] | qs to 100% | qs to 100% | qs to 100% |
| pH of a 10% aqueous solution adjusted to | 9.3 | 8.5 | 11 |

[1]$E_9$ Ethoxylated Alcohols as sold by the Shell Oil Co.
[2]1,3-bis(methylamino)cyclohexane.
[3]Diethylenetriaminepentaacetate.
[4]Suitable protease enzymes include Savinase ®; Maxatase ®; Maxacal ®; Maxapem 15 ®; subtilisin BPN and BPN'; Protease B; Protease A; Protease D; Primase ®; Durazym ®; Opticlean ®; and Optimase ®; and Alcalase ®.
[5]Suitable amylase enzymes include Termamyl ®, Fungamyl ®; Duramyl ®; BAN ®, and the amylases as described in WO95/26397 and in co-pending application by Novo Nordisk PCT/DK/96/00056.
[6]Suitable hydrotropes include sodium, potassium, ammonium or water-soluble substituted ammonium salts of toluene sulfonic acid, naphthalene sulfonic acid, cumene sulfonic acid, xylene sulfonic acid.
[7]Includes perfumes, dyes, ethanol, etc.

Example 12

A disposable child sized article according to Example 10, except that the LDL is selected from one of P, Q, R or S.

| | weight % | | | |
|---|---|---|---|---|
| Ingredients | P | Q | R | S |
| $C_{12}$-$C_{15}$ Alkyl ($E_1$) sulfate | — | 30.0 | — | — |
| $C_{12}$-$C_{15}$ Alkyl ($E_{1.4}$) sulfate | 30.0 | — | 27.0 | — |
| $C_{12}$-$C_{15}$ Alkyl ($E_{2.2}$) sulfate | — | — | — | 15 |
| $C_{12}$ Amine oxide | 5.0 | 5.0 | 5.0 | 3.0 |
| $C_{12}$-$C_{14}$ Betaine | 3.0 | 3.0 | — | — |
| $C_{10}$ Alcohol Ethoxylate $E_9$[1] | 2.0 | 2.0 | 2.0 | 2.0 |
| Diamine[2] | 1.0 | 2.0 | 4.0 | 2.0 |
| $Mg^{2+}$ (as $MgCl_2$) | 0.25 | 0.25 | — | — |
| $Ca^{2+}$ (as Ca(citrate)$_2$) | — | 0.4 | — | — |
| Polymeric suds booster[3] | 0.5 | 1.0 | 0.75 | 5.0 |
| Minors and water[4] | qs to 100% | qs to 100% | qs to 100% | qs to 100% |
| pH of a 10% aqueous solution adjusted to | 7.4 | 7.6 | 7.4 | 7.8 |

[1] $E_9$ Ethoxylated Alcohols as sold by the Shell Oil Co.
[2] 1,3-diaminopentane sold as Dytek EP.
[3] LX1279 available from Baker Petrolite.
[4] Includes perfumes, dyes, ethanol, etc.

Example 13

A disposable child sized article wherein the nonwoven sheet member is a two-layer laminate. The first layer of the laminate is a 40 gsm PET spunlace. While the second layer of the laminate is a 60 gsm polyester nonwoven high loft batting material, Proef 1297 available from Libeltex of Meulebeke Belgium. Disposed on one side of the nonwoven high loft batting material is the child graphic illustrated in FIG. 22. Disposed on the other side of the nonwoven high loft batting material is retaining aid which is illustrated in FIG. 3. The high loft batting material is also releasably carrying 30 gsm of the benefit composition, which is a hair care composition, specifically one of T, U, V or W.

| | T | U | V | W |
|---|---|---|---|---|
| Disodium Lauroamphodiacetate | 0.6 | 0.6 | 0.6 | 0.6 |
| Sodium Trideceth Sulfate | 3.0 | 3.0 | 3.0 | 3.0 |
| PEG-6 Cocamide | — | 1.0 | — | — |
| PEG-6 Lauramide | — | — | 1.0 | — |
| PEG-3 Cocamide | — | — | — | 1.0 |
| Quaternium-22 | 0.37 | 0.37 | 0.37 | 0.37 |
| Glycerin | 1.9 | 1.9 | 1.9 | 1.9 |
| PEG-120 Methyl Glucose Dioleate | 1.0 | 1.0 | 1.0 | 1.0 |
| POE 80 Sorbitan Monolaurate | 3.3 | 3.3 | 3.3 | 3.3 |
| Sodium Laureth-13 Carboxylate | 0.23 | 0.23 | 0.23 | 0.23 |
| Polyquaternium 10 | 0.14 | 0.14 | 0.14 | 0.14 |
| Cocamidopropyl Betaine | 2.8 | 2.8 | 2.8 | 2.8 |
| Tetrasodium EDTA | 0.10 | 0.10 | 0.10 | 0.10 |
| Quaternium 15 | 0.05 | 0.05 | 0.05 | 0.05 |
| Citric Acid, USP | 0.10 | 0.10 | 0.10 | 0.10 |
| Water | Quantity sufficient | | | |

Example 14

A disposable child sized article wherein the nonwoven sheet member is a 60 gsm polyester nonwoven high loft batting material, Proef 1297 available from Libeltex of Meulebeke Belgium. Disposed on one side of the nonwoven high loft batting material are the child graphic illustrated in FIGS. 22 and 24. Disposed on the other side of the nonwoven high loft batting material is retaining aid which is illustrated in FIG. 4. The high loft batting material is also releasably carrying 35 gsm of the benefit composition, which is a sunscreen composition, which is made as follows. An emulsifier or water-insoluble phase is prepared by blending, at room temperature, cetyl dimethicone copolyol, polyglyceryl-3-distearate, polyglyceryl-4 isostearate, cetyl dimethyl copolyol, hexyl laurate, caprylic and/or capric triglyceride, propylparaben, methylparaben, p-methoxycinnamate, ethylhexyl salicylate, oxybenzone, minor ingredients, and about 0.12% by emulsion weight of a color blend of D&C Green #6, D&C Red #12, and D&C Violet #2 in suitable proportions to make a purple emulsion. Separately, an aqueous phase is prepared by combining, at room temperature, deionized water, aloe vera gel, sodium chloride, chamomile extract, ascorbic acid (Vitamin C), and minor ingredients.

The two phases are then combined by adding the water phase to the emulsifier phase with constant mixing. The mixture is then homogenized with a suitable homogenizing mill until the required viscosity is reached.

The resulting sunscreen is applied to the nonwoven member.

Example 15

A disposable child sized article wherein the nonwoven sheet member is a 60 gsm polyester nonwoven high loft batting material, Proef 1297 available from Libeltex of Meulebeke Belgium. Disposed on both sides of the nonwoven high loft batting material is the child graphic illustrated in FIG. 25. Disposed on the other side of the nonwoven high loft batting material is retaining aid which is illustrated in FIG. 6. The high loft batting material is also releasably carrying 35 gsm of the benefit composition, which is a haircare composition, specifically one of X, Y, Z, AA or BB.

About one-third to all of the total sulfate surfactant (added as a 25% solution) is added to a jacketed mix tank and heated to about 74° C. with slow agitation to form a surfactant solution. Cocamide MEA and fatty alcohol, as applicable, are added to the tank and allowed to disperse. Ethylene glycol distearate (EGDS), as applicable, is then added to the mixing vessel, and melted. After the EGDS is well dispersed (usually about 5 to 20 minutes) polyethylene glycol and the preservative, if used are added and mixed into the surfactant solution. This mixture is passed through a heat exchanger where it is cooled to about 35° C. and collected in a finishing tank. As a result of this cooling step, the ethylene glycol distearate crystallizes to form a crystalline network in the product. The remainder of the surfactant and other ingredients including the silicone emulsions are added to the finishing tank with ample agitation to insure a homogeneous mixture. A sufficient amount of the silicone emulsions are added to provide the desired level of dimethicone in the final product. Water dispersible polymers are typically dispersed in water as a 1% to 10% solution before addition to the final mix. Once all ingredients have been added, ammonium xylene sulfonate or additional sodium chloride can be added to the mixture to thin or thicken respectively to achieve a desired product viscosity. Preferred viscosities range from about 2500 to about 9000 cS at 25° C. (as measured by a Wells-Brookfield cone and plate viscometer at 15/s). The resulting composition is then applied to the nonwoven member.

| Component (% by weight) | X | Y | Z | AA | BB |
|---|---|---|---|---|---|
| Ammonium AES[1] | 9.00 | 9.00 | 14.0 | 14.85 | 12.50 |
| Cocamidopropylbetaine | 1.70 | 1.70 | 2.70 | 1.85 | 4.20 |
| Polyquaternium-10[2] | 0.05 | 0.02 | 0.15 | 0.15 | 0.15 |
| Cocamide MEA | 0.80 | 0.80 | 0.80 | 0.80 | 0 |
| Cetyl Alcohol | 0 | 0 | 0.42 | 0.42 | 0.42 |
| Stearyl Alcohol | 0 | 0 | 0.18 | 0.18 | 0.18 |
| Ethylene Glycol Distearate | 1.50 | 1.50 | 1.50 | 1.50 | 1.50 |
| EP Silicone[3] | 3.0 | 2.5 | 3.0 | 2.0 | 3.0 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | | | q.s. to 100% | | |

[1]Ammonium Laureth sulfate having an average ethoxylation of about 3 EO.
[2]Polyquaternium-10 is JR30M, a cationic cellulose derived polymer available from Amerchol.
[3]EP Silicone is an experimental emulsion polymerized polydimethyl siloxane of about 335,000 csk with particle size of approximately 500 nm made via linear feedstock available from Dow Corning (2-1520; PE106004).

Example 16

A disposable child sized article wherein the nonwoven sheet member is a 60 gsm polyester nonwoven high loft batting material, Proof 1297 available from Libeltex of Meulebeke Belgium. Disposed on one side of the nonwoven high loft batting material is the child graphic illustrated in FIG. 20. Disposed on the other side of the nonwoven high loft batting material is retaining aid which is illustrated in FIG. 2. The high loft batting material is also releasably carrying 35 gsm of the benefit composition, which is a sunscreen composition, comprising, water, Titanium Dioxide, Xanthan Gum, Cocamide DEA, Neodol 1-7, Neodol 25-7, C12-15 Amine Oxide, glycerin, IPBC, 10,000 cSt. Silicone Fluid, Silicone Antifoam Emulsion, Fragrance2-ethylhexyl-p-methoxycinnamate, 2,2'-dihydroxy4,4'-dimethoxybenzophenone, zinc oxide, and polyacrtlamide.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable child sized personal cleaning article comprising:
   (a) a nonwoven sheet member;
   (b) retaining aid disposed on said nonwoven sheet member, said retaining aid enables a child to retain said article on a hand of said child;
   (c) between 0.5 g and 20 g of a lathering benefit composition, the benefit composition comprising at least one of a paste and a dry solid having less than 50 % moisture by way of the benefit composition and a surfactant, wherein said nonwoven sheet member is releasably carrying said benefit composition; and
   (d) a child graphic disposed on said nonwoven member.

2. The disposable child sized article according to claim 1 wherein said benefit composition is selected from the group consisting of cleaning compositions, moisturizing compositions, medicinal compositions, cosmetic compositions, personal cleansing compositions, polishing compositions, automotive cleaning compositions, germicidal compositions, wax compositions, perfume compositions, dishwashing compositions, hard surface cleaning compositions, glass cleaning compositions, and wood cleaning compositions.

3. The disposable child sized article according to claim 1 wherein said nonwoven member is retained on the palm of said hand of said child.

4. The disposable child sized article according to claim 1 wherein said retaining aid is selected from the group consisting of an elastic member, finger loop, thumb loop, wrist band, pocket, adhesive tape, and combinations thereof.

5. The disposable child sized article according to claim 1 wherein said child graphic is in the form of at least one of photographs, drawings, cartoons, symbols and combinations thereof.

6. The disposable child sized article according to claim 1 wherein said child graphic is appealing to a child of from about three years old to about five years old.

7. The disposable child sized article according to claim 1 wherein said child graphic is appealing to a child of from about six years old to about nine years old.

8. The disposable child sized article according to claim 1 wherein said child graphic is selected from the group consisting of graphics appealing to girls, graphics appealing to boys gender neutral graphics and combinations thereof.

9. The disposable child sized article according to claim 1 wherein said child graphic comprises a character graphic.

10. The disposable child sized article according to claim 9 wherein said character graphic is in the form of drawings, cartoons, symbols or combinations thereof.

11. The disposable child sized article according to claim 9 wherein said character graphic is selected from the group consisting of graphics appealing to girls, graphics appealing to boys gender neutral graphics and combinations thereof.

12. The disposable child sized article according to claim 9 wherein said character graphic is appealing to a child of from about three years old to about five years old.

13. The disposable child sized article according to claim 9 wherein said character graphic is appealing to a child of from about six years old to about nine years old.

14. The disposable child sized article according to claim 9 wherein said character graphic is selected from the group consisting of animals, objects and combinations thereof 15. The disposable child sized article according to claim 1 wherein said child graphic is a registered graphic.

16. The disposable child sized article according to claim 1 wherein said disposable child sized article is one component of a system of consumer products.

17. The disposable child sized article according to claim 1 wherein said child graphic is a cartoon of an animal selected from the group consisting of amphibians, turtles, monkeys, automobiles and combination thereof.

18. A disposable child sized personal cleaning article comprising:
   (a) a nonwoven sheet member;
   (b) retaining aid disposed on said nonwoven sheet member, said retaining aid enables a child to retain said article on a hand of said child;
   (c) between 0.5 g and 20 g of a lathering benefit composition, the benefit composition comprising at least one of a paste and a dry solid having less than 50% moisture by way of the benefit composition and a surfactant, wherein said nonwoven sheet member is releasably carrying said benefit composition; and
   (d) a child graphic disposed on said nonwoven member; and
   (e) a usage indicator.

19. The disposable child sized article according to claim 18 wherein said usage indicator is selected from the group consisting of pH change indicator, a temperature change indicator, time change indicator and combinations thereof.

20. The disposable child sized article according to claim 18 wherein said usage indicator provides a visual signal during use of said article that at least a portion of said benefit composition has been released from said nonwoven member.

21. The disposable child sized article according to claim 18 wherein said usage indicator is a child graphic.

* * * * *

UNITED STATES PATENT AND TRADEMARK OFFICE
CERTIFICATE OF CORRECTION

PATENT NO. : 7,490,382 B2
APPLICATION NO. : 10/948491
DATED : February 17, 2009
INVENTOR(S) : Joyce Marie Benjamin et al.

It is certified that error appears in the above-identified patent and that said Letters Patent is hereby corrected as shown below:

Column 10

Line 35, delete "20." and insert -- 20 --.

Column 28

Line 13, delete "way" and insert -- weight --.

Line 46, after "boys" insert -- , --.

Line 47, after "graphics" insert -- , --.

Line 56, after "boys" insert -- , --.

Line 56, after "graphics" insert -- , --.

Column 30

Line 1, delete "way" and insert -- weight --.

Signed and Sealed this

Fifteenth Day of September, 2009

David J. Kappos
*Director of the United States Patent and Trademark Office*